(12) United States Patent
Netherton

(10) Patent No.: US 11,857,780 B2
(45) Date of Patent: Jan. 2, 2024

(54) ADJUSTABLE NERVE PROBE ASSEMBLY

(71) Applicant: ROCWORKS, LLC, Prosperity, SC (US)

(72) Inventor: Brett Netherton, Prosperity, SC (US)

(73) Assignee: ROCWORKS, LLC, Prosperity, SC (US)

( * ) Notice: Subject to any disclaimer, the term of this patent is extended or adjusted under 35 U.S.C. 154(b) by 772 days.

(21) Appl. No.: 16/959,640

(22) PCT Filed: Jan. 2, 2019

(86) PCT No.: PCT/IB2019/050037
§ 371 (c)(1),
(2) Date: Jul. 1, 2020

(87) PCT Pub. No.: WO2019/135185
PCT Pub. Date: Jul. 11, 2019

(65) Prior Publication Data
US 2021/0077809 A1  Mar. 18, 2021

Related U.S. Application Data

(60) Provisional application No. 62/612,863, filed on Jan. 2, 2018.

(51) Int. Cl.
*A61N 1/05* (2006.01)
*A61B 5/24* (2021.01)
*A61B 5/00* (2006.01)

(52) U.S. Cl.
CPC .............. *A61N 1/0551* (2013.01); *A61B 5/24* (2021.01); *A61B 5/4041* (2013.01); *A61B 5/4893* (2013.01); *A61B 2562/0209* (2013.01); *A61B 2562/16* (2013.01)

(58) Field of Classification Search
CPC ...... A61N 1/0551; A61B 5/24; A61B 5/4041; A61B 5/4893; A61B 2562/0209; A61B 2562/16
See application file for complete search history.

(56) References Cited

U.S. PATENT DOCUMENTS

| 5,551,426 A | 9/1996 | Hummel et al. |
| 2006/0106296 A1 | 5/2006 | Mejia |
| 2011/0098704 A1 | 4/2011 | Long et al. |
| 2012/0150063 A1 | 6/2012 | Rea |
| 2014/0330354 A1 | 11/2014 | Shelton et al. |
| 2015/0119674 A1 | 4/2015 | Fischell et al. |

*Primary Examiner* — Mark W. Bockelman
(74) *Attorney, Agent, or Firm* — BURR & FORMAN LLP

(57) ABSTRACT

Electrical probe assemblies, such as nerve probe assemblies, are disclosed herein. In one example implementation, a nerve probe assembly may include an electrical probe including an electrode disposed on or about an end thereof for electrically stimulating tissue or recording stimulated tissue activity, an axial length of the electrical probe including a shapeable part; a rigid sheathing adapted to cover and thereby inhibit a portion of the shapeable part of the axial length of the electrical probe from being shaped, the portion of the shapeable part covered by the rigid sheathing being adjustable; and a handle and an adjustment structure affixed to respective ones of the electrical probe and the rigid sheathing, the handle and the adjustment structure adapted to cooperate to enable adjustment of the portion of the shapeable part of the axial length of the electrical probe covered by the rigid sheathing.

20 Claims, 12 Drawing Sheets

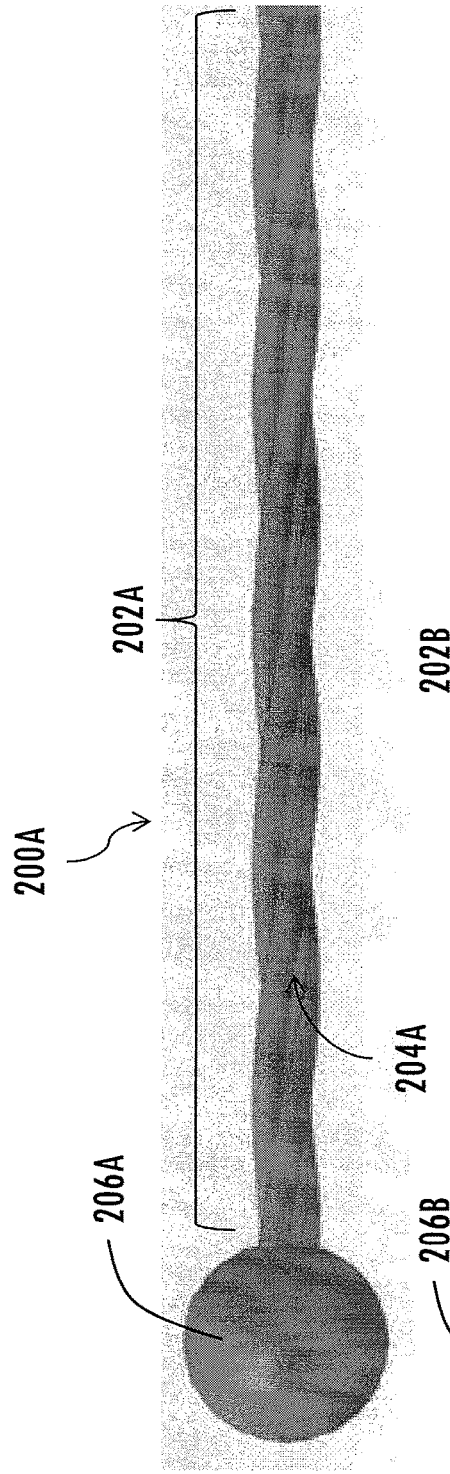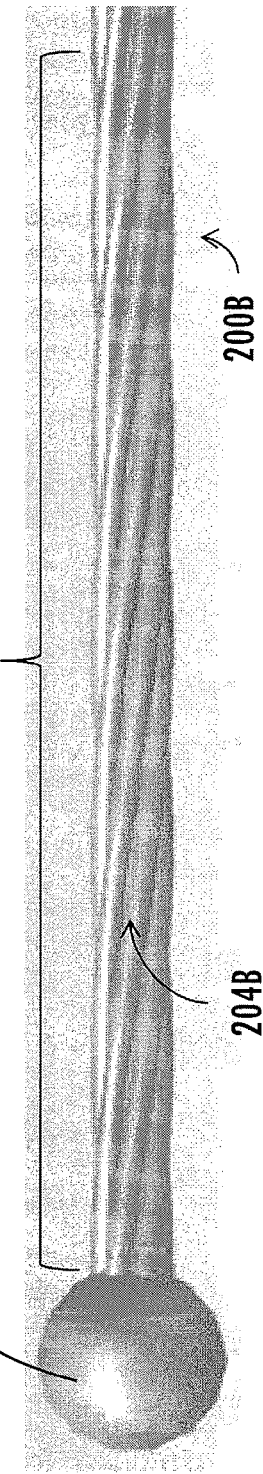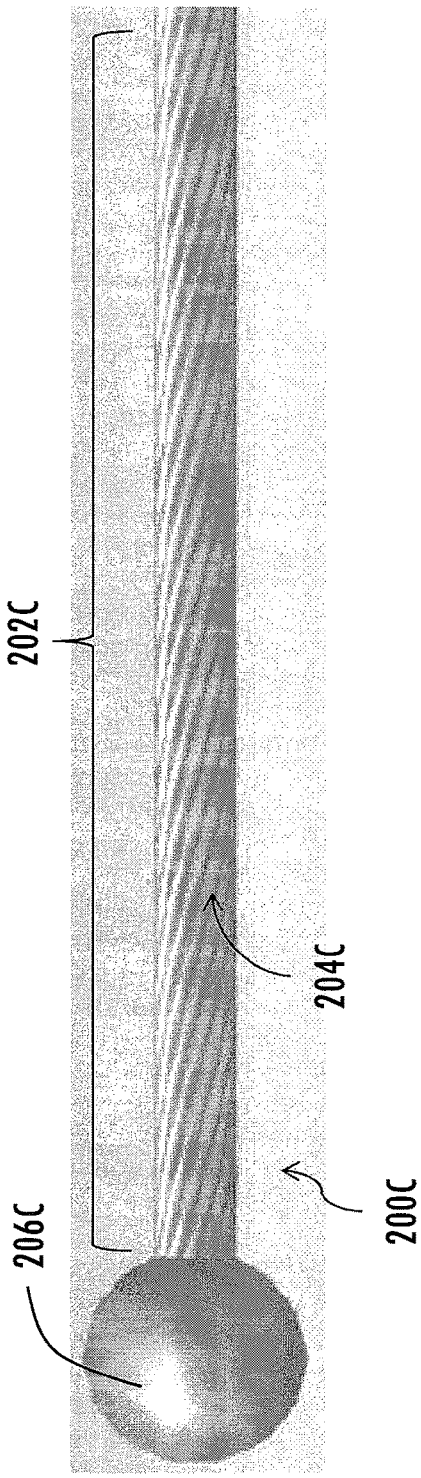

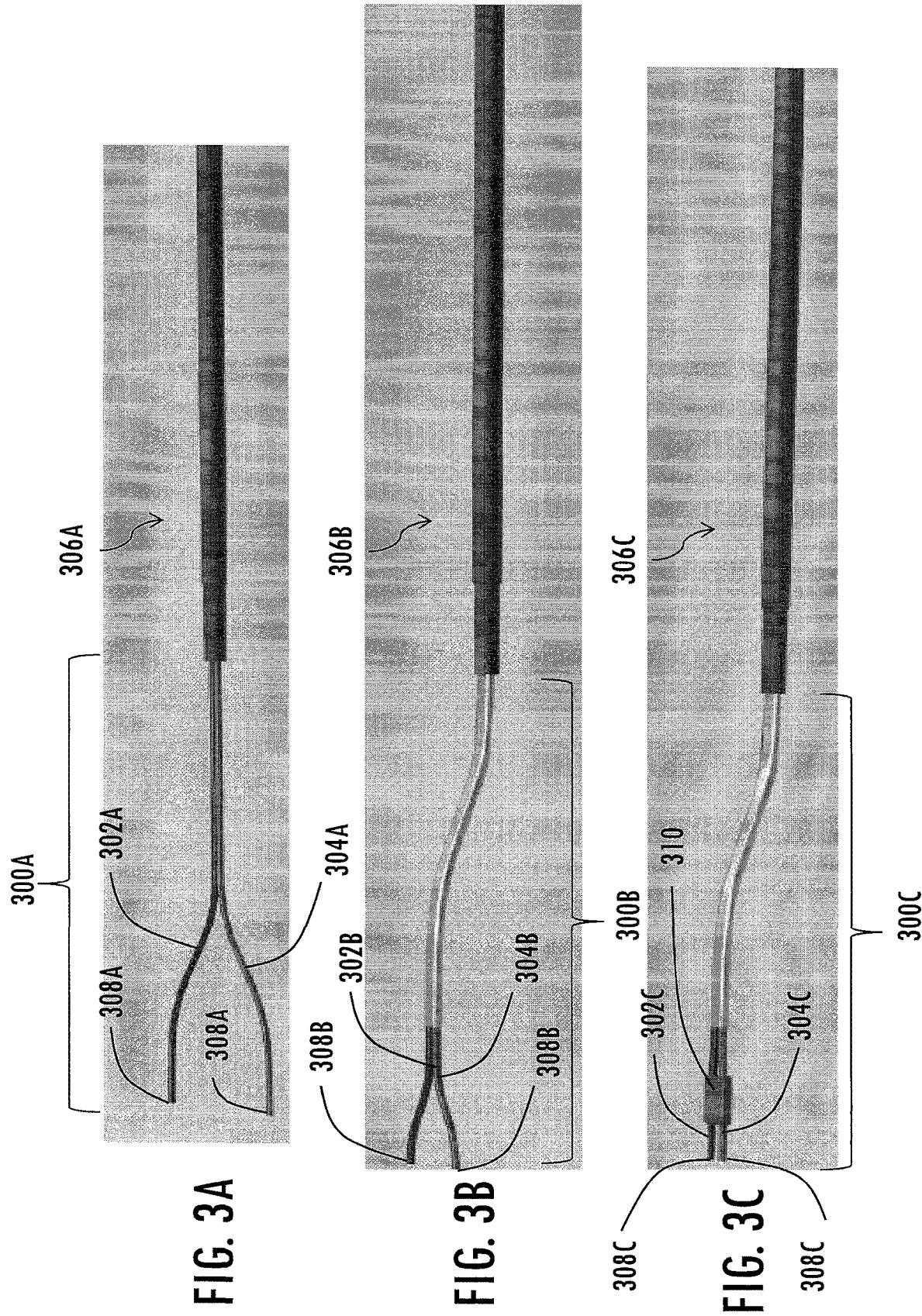

Figure 1:
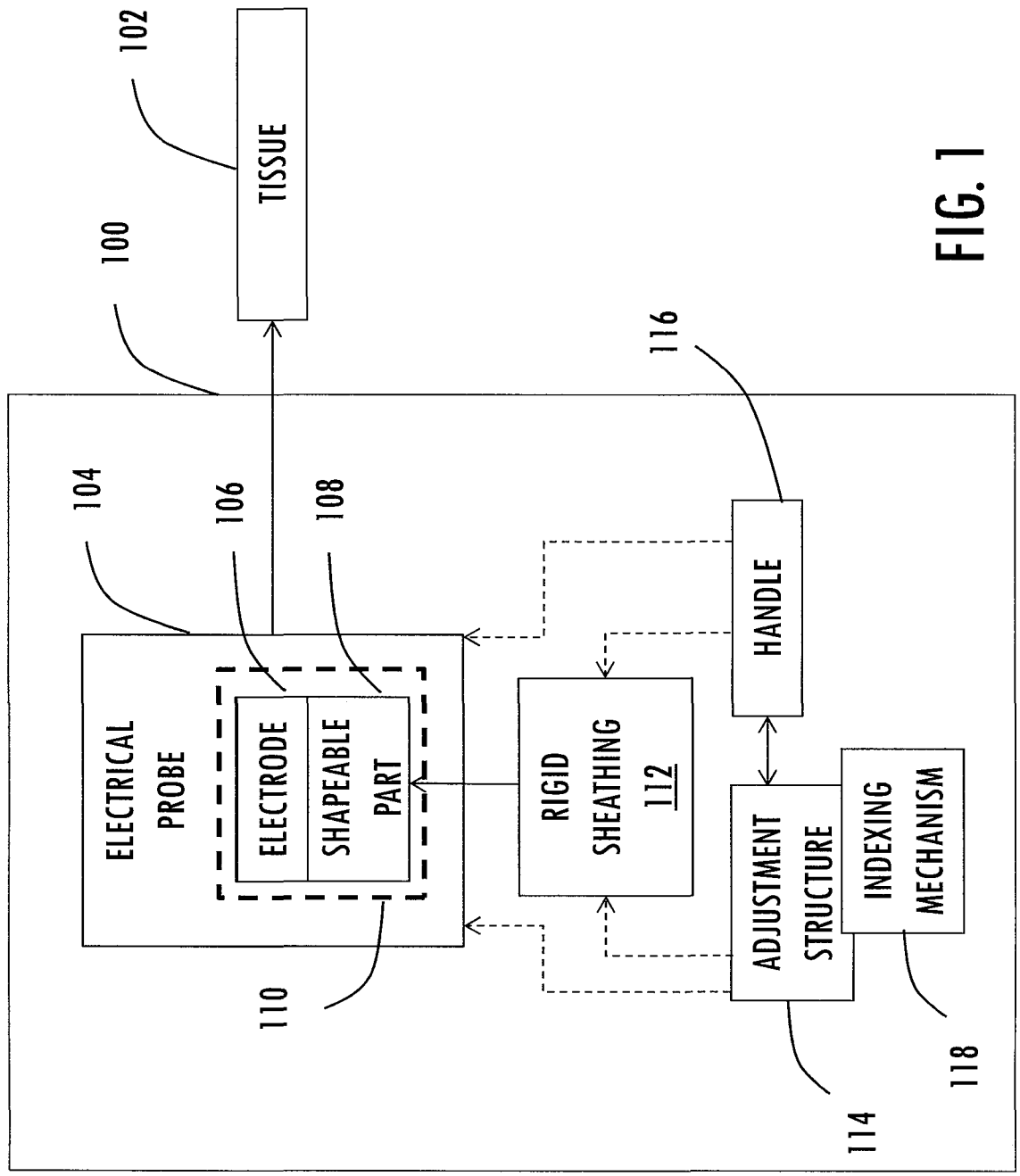

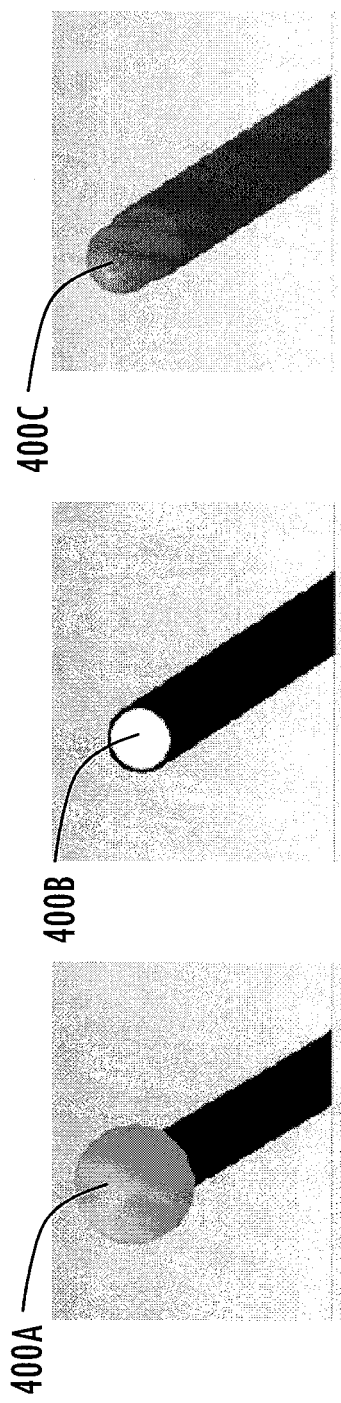
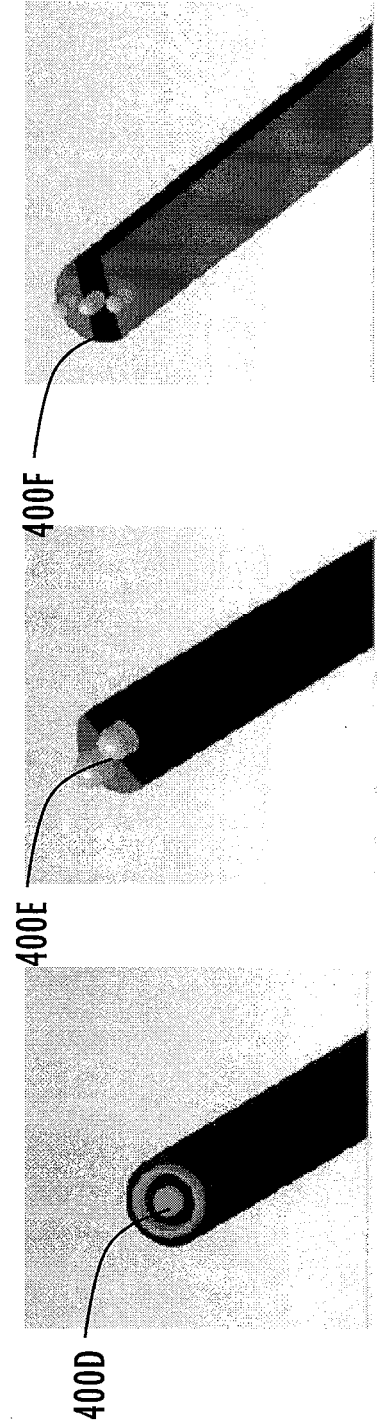

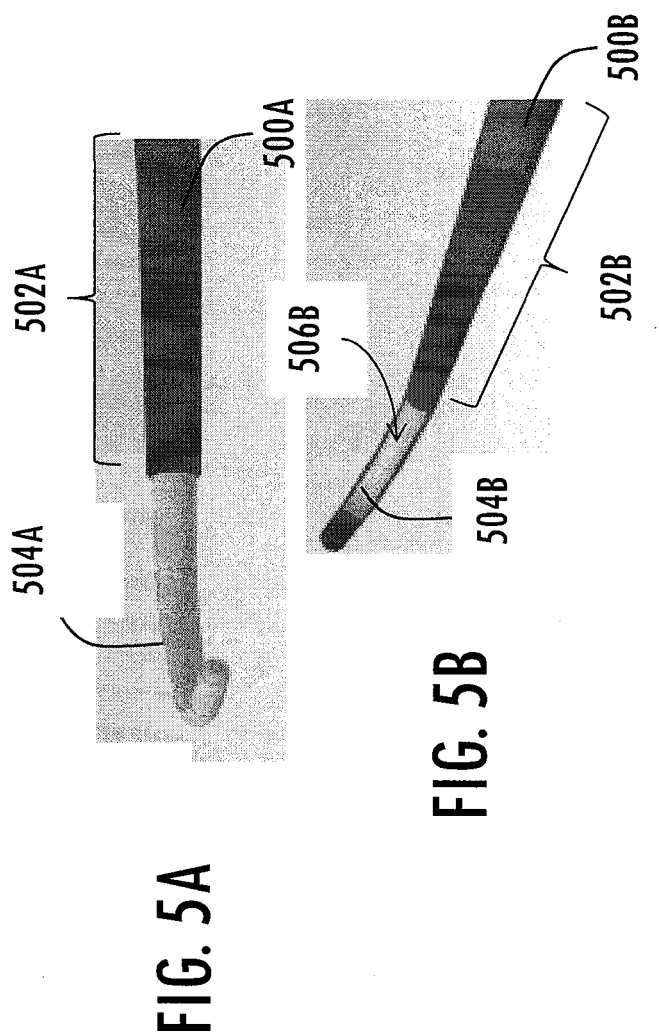

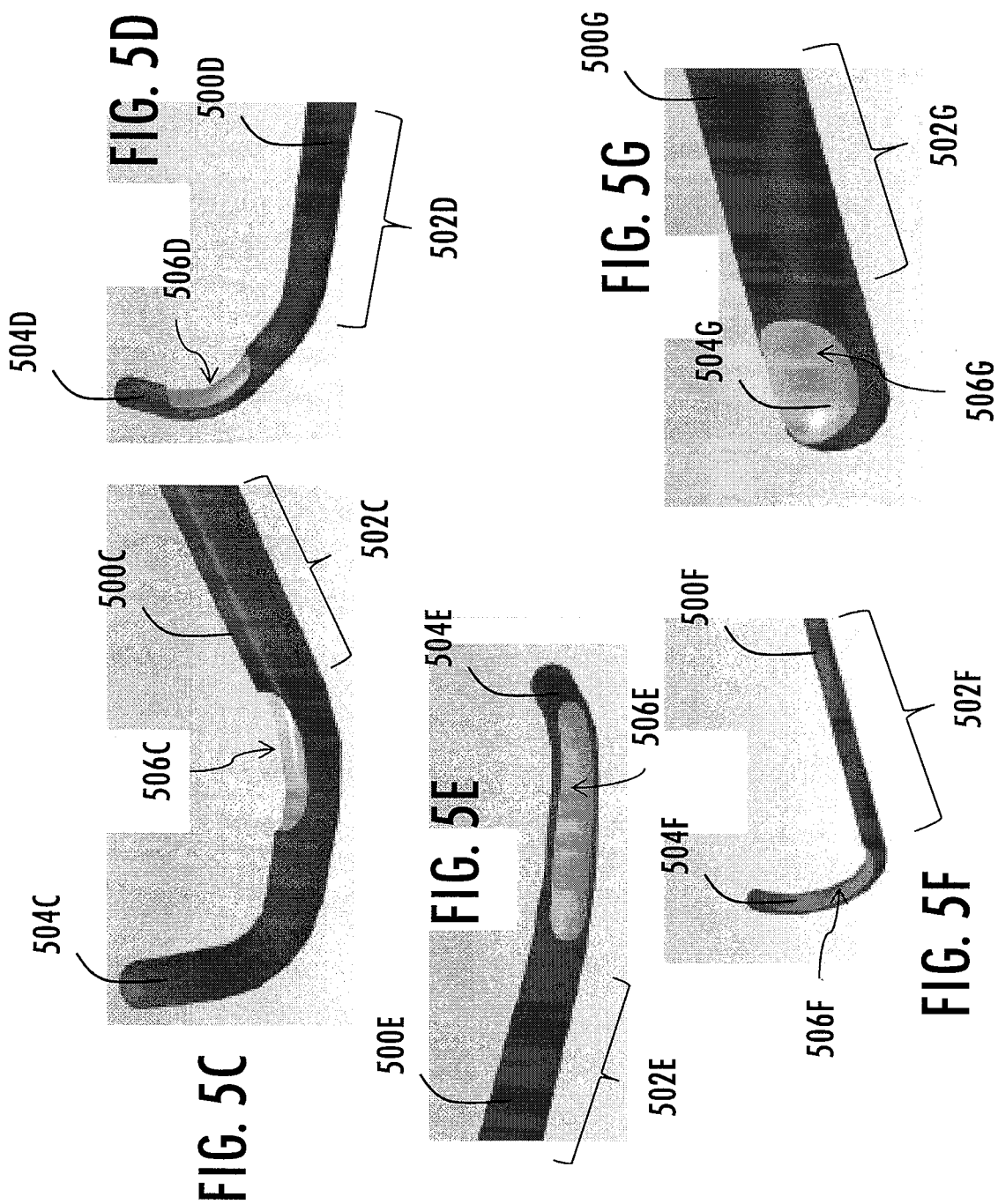

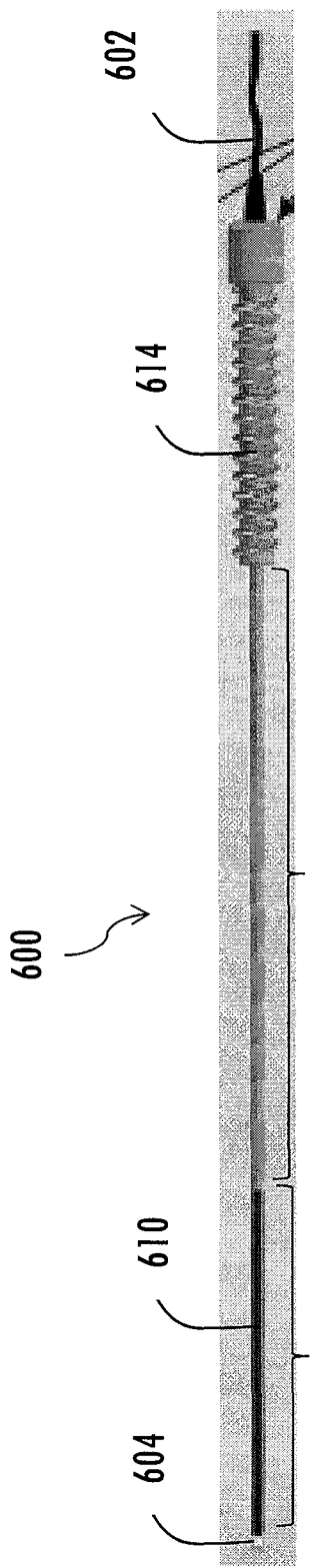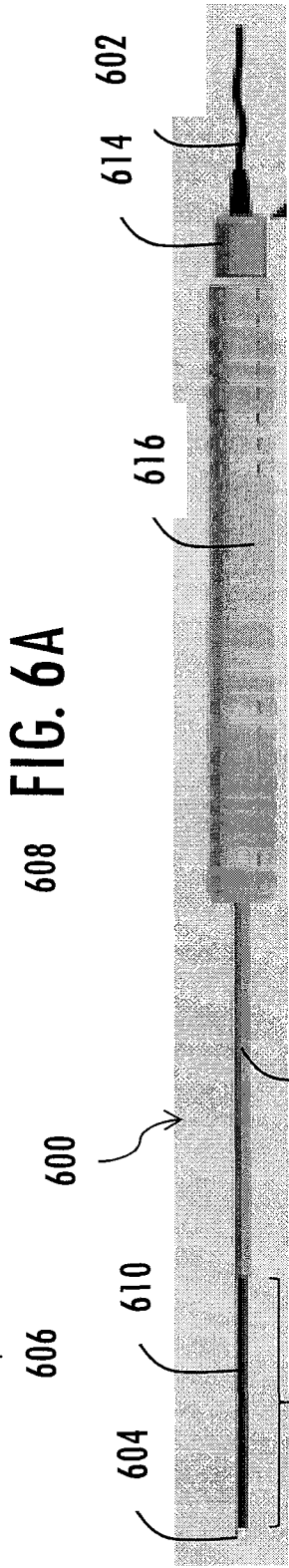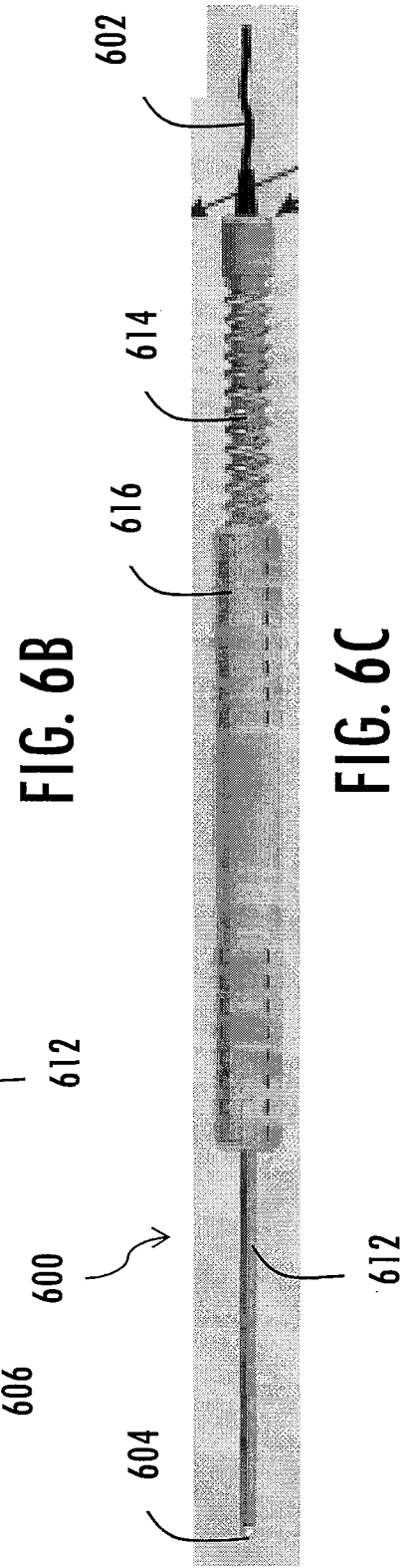

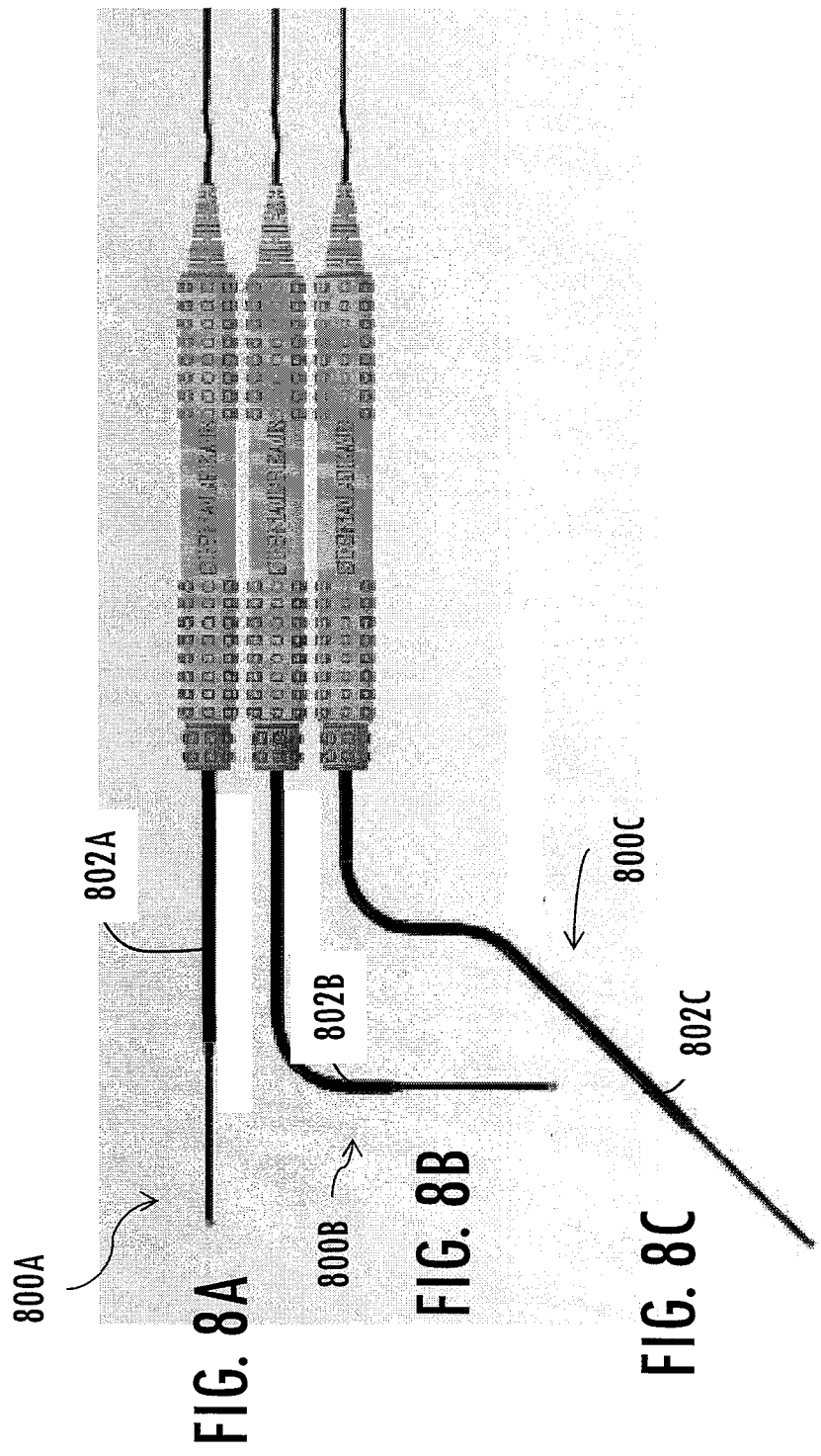

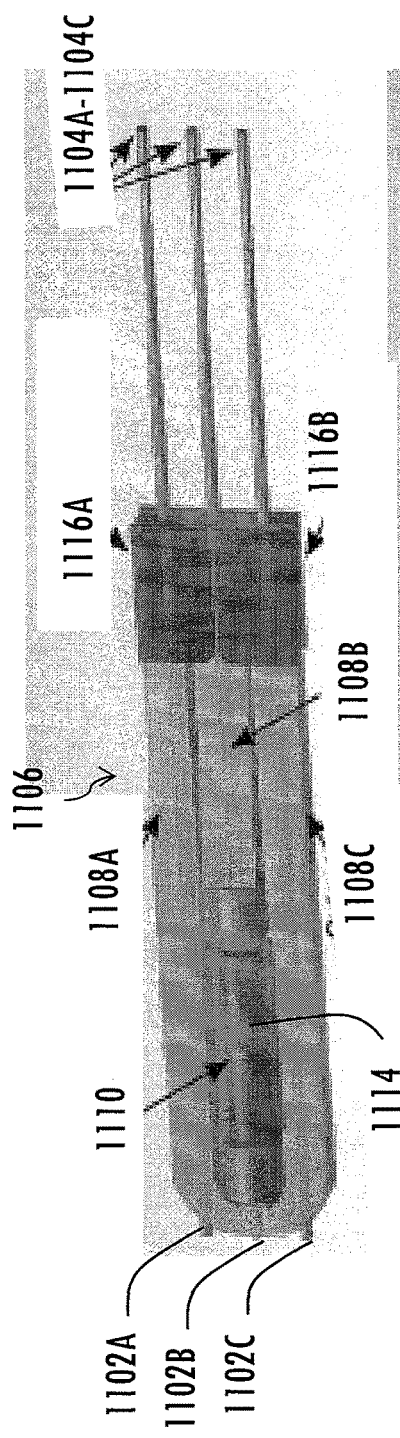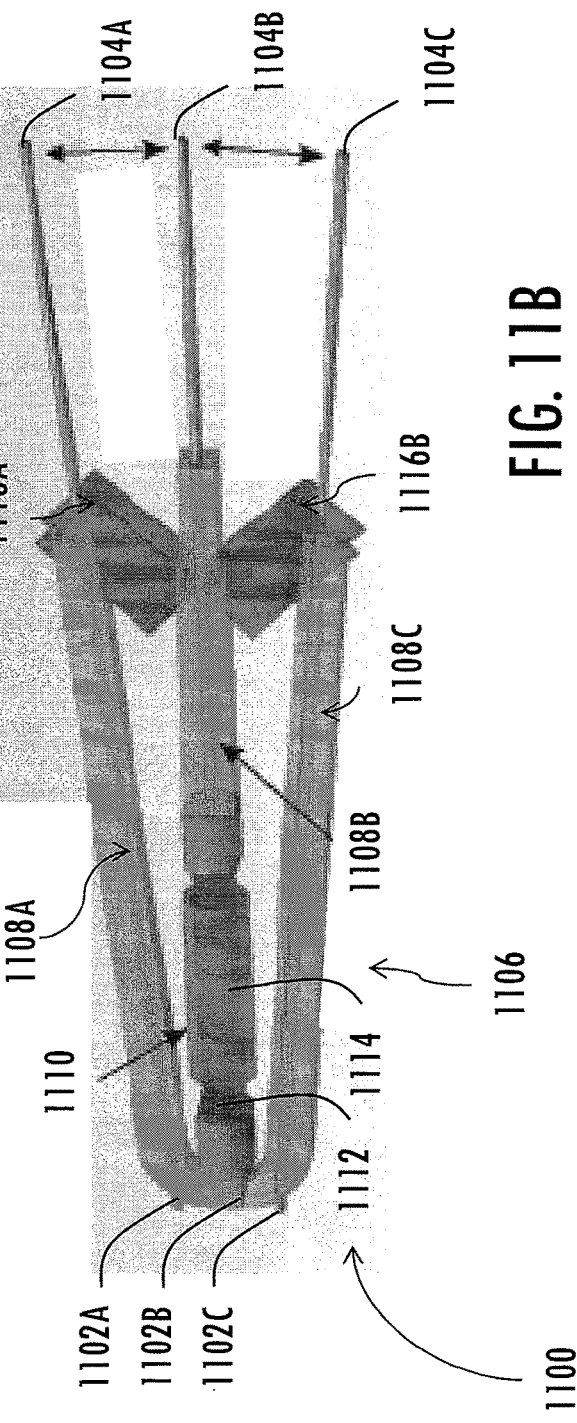

ADJUSTABLE NERVE PROBE ASSEMBLY

CROSS-REFERENCE TO RELATED APPLICATIONS

This application is a national stage filing under 35 U.S.C. § 371 of PCT/IB2019/050037, filed on Jan. 2, 2019, which International Application was published by the International Bureau in English on Jul. 11, 2019 as WO 2019/135185, and application claims priority from U.S. Provisional Application No. 62/612,863, filed on Jan. 2, 2018, which applications are hereby incorporated by reference in their entirety in this application.

TECHNOLOGICAL FIELD

The present disclosure relates generally to electrical probes and, in particular, to adjustable nerve probe assemblies for electrically stimulating tissue and/or recording stimulated tissue activity.

BACKGROUND

Stimulation probes have been used for decades in many types of surgery. With the exception of bone, fat, tendon, and other sinew-type tissues, human tissues tend to have significant conductivity. For surgeons electrically searching for a neural structure of interest (e.g., human tissue), this conductivity can be advantageous because it may allow the use of electrical stimulation and recordation for localization and identification purposes. However, tissue conductivity may be a detriment since conductive pathways between a stimulation point and a recording point may introduce an opportunity for erroneous false positives, which is undesirable.

For example, if a target muscle innervated by a nerve is electrically stimulated so that the muscle is activated, there may be an increased certainty of nerve identification However, if a neighboring nerve is accidentally electrically stimulated and the current finds a low conductivity pathway directly to the target muscle, the target muscle may be accidentally electrically stimulated (without actually stimulating the nerve that innervates that target muscle), thereby resulting in a false positive nerve identification.

As such, stimulating a neural structure of interest using stimulation probes is a complex skill. Surgeons skilled in the use of electrical stimulation techniques may need numerous different stimulation probes to reach various structures of interest depending on many anatomical and surgical variables. Therefore, it is desirable that stimulation probes be multiple and variate in form.

Accordingly, it may be desirable to have an adjustable electrical probe assembly for electrically stimulating an object or recording stimulated object activity, the object being, for example, tissue, which addresses the issues noted herein.

BRIEF SUMMARY

Example implementations of the present disclosure are directed to an electrical probe assembly for electrically stimulating an object or recording stimulated object activity, the object being, for example, but not limited to, tissue. The electrical probe assembly may include a shapeable part shapeable to different shapes and an adjustment structure that is arranged to adjust a portion of the shapeable part of an axial length of the electrical probe covered by a rigid sheathing so as to vary flexibility of the electrical probe and allow shaping of the shapeable part to different shapes. The adjustment structure may also be arranged to adjust a distance between two or more electrodes.

The present disclosure thus includes, without limitation, the following example implementations.

Some example implementations provide a nerve probe assembly comprising an electrical probe including an electrode disposed on or about an end thereof for electrically stimulating tissue or recording stimulated tissue activity, an axial length of the electrical probe including a shapeable part; a rigid sheathing adapted to cover and thereby inhibit a portion of the shapeable part of the axial length of the electrical probe from being shaped, the portion of the shapeable part covered by the rigid sheathing being adjustable; and a handle and an adjustment structure affixed to respective ones of the electrical probe and the rigid sheathing, the handle defining an internal cavity sized to fit the adjustment structure, the handle and the adjustment structure adapted to cooperate to enable adjustment of an amount of the adjustment structure that extends out of the handle, and thereby adjustment of the portion of the shapeable part of the axial length of the electrical probe covered by the rigid sheathing.

In some example implementations of the nerve probe assembly of any preceding example implementation, or any combination of any preceding example implementations, the electrode may be shaped as a rounded tip electrode, a flush tip electrode, or a ball tip electrode.

In some example implementations of the nerve probe assembly of any preceding example implementation, or any combination of any preceding example implementations, the electrode may define a single electrode or two or more electrodes.

In some example implementations of the nerve probe assembly of any preceding example implementation, or any combination of any preceding example implementations, the electrode may define the two or more electrodes, and the two or more electrodes include a stimulation electrode for electrically-stimulating tissue, and a recording electrode for recording activity of the stimulated tissue.

In some example implementations of the nerve probe assembly of any preceding example implementation, or any combination of any preceding example implementations, the electrode may define the two or more electrodes, and the two or more electrodes are arranged as concentric electrodes or side-by-side electrodes.

In some example implementations of the nerve probe assembly of any preceding example implementation, or any combination of any preceding example implementations, the electrical probe may include an electrically-insulating sheathing that extends along the axial length of the electrical probe.

In some example implementations of the nerve probe assembly of any preceding example implementation, or any combination of any preceding example implementations, the electrode of the electrical probe may be disposed on the end of the electrical probe, and the electrically-insulating sheathing may extend along the axial length of the electrical probe up to but not including the end so that only the electrode is exposed.

In some example implementations of the nerve probe assembly of any preceding example implementation, or any combination of any preceding example implementations, the electrode may be disposed about the end of the electrical probe, and the electrically-insulating sheathing may extend along the axial length of the electrical probe up to and including the end, and around at least a portion of the electrode so that only the other portion of the electrode is exposed.

In some example implementations of the nerve probe assembly of any preceding example implementation, or any combination of any preceding example implementations, the nerve probe assembly may further comprise an indexing mechanism that may be coupled to or integrated with the adjustment structure and arranged to index the adjustment structure in a plurality of predetermined positions relative to the handle, including an extended position in which a maximum amount of the adjustment structure extends out of the handle, a retracted position in which a minimum amount of the adjustment structure extends out of the handle, and at least one intermediate position therebetween.

In some example implementations of the nerve probe assembly of any preceding example implementation, or any combination of any preceding example implementations, the electrical probe and the rigid sheathing may be affixed to respectively the handle and the adjustment structure.

In some example implementations of the nerve probe assembly of any preceding example implementation, or any combination of any preceding example implementations, the electrical probe and the rigid sheathing may be affixed to respectively the adjustment structure and the handle.

In some example implementations of the nerve probe assembly of any preceding example implementation, or any combination of any preceding example implementations, the adjustment structure may comprise a threaded insert, and the internal cavity of the handle may define a corresponding interior thread adapted to threadably engage the threaded insert, and the threaded insert may be rotatable within the internal cavity with the corresponding interior thread to adjust the amount of the threaded insert that extends out of the handle, and thereby adjust the portion of the shapeable part of the axial length of the electrical probe covered by the rigid sheathing.

In some example implementations of the nerve probe assembly of any preceding example implementation, or any combination of any preceding example implementations, the threaded insert may be rotatable to a plurality of positions including an extended position in which a maximum amount of the threaded insert extends out of the handle, and thereby a maximum portion of the shapeable part is covered by the rigid sheathing, and a retracted position in which a minimum amount of the threaded insert extends out of the handle, and thereby a minimum portion of the shapeable part is covered by the rigid sheathing.

In some example implementations of the nerve probe assembly of any preceding example implementation, or any combination of any preceding example implementations, the plurality of positions may further include at least one intermediate position between the extended position and the retracted position in which the amount of the threaded insert that extends out of the handle is between the maximum amount and the minimum amount, and thereby the portion of the shapeable part covered by the rigid sheathing is between the maximum portion and the minimum portion.

In some other example implementations, a nerve probe assembly comprises first and second electrical probes including first and second electrodes disposed on or about respective ends thereof for electrically stimulating tissue or recording stimulated tissue activity; a handle including first and second arms adapted to carry respectively the first and second electrical probes, the first and second arms including respective ends from which the first and second electrical probes extend; and an adjustment structure coupled to the first arm or the second arm, and adapted to enable adjustment of a distance between the respective ends of the first and second arms, and thereby adjust a corresponding distance between the first and second electrodes.

In some example implementations of the nerve probe assembly of any preceding example implementation, or any combination of any preceding example implementations, the nerve probe assembly may further comprise a third electrical probe including a third electrode disposed on or about an end thereof for electrically stimulating tissue or recording stimulated tissue activity, wherein the handle further includes a third arm adapted to carry the third electrical probe, the third arm including an end from which the third electrical probe extends.

In some example implementations of the nerve probe assembly of any preceding example implementation, or any combination of any preceding example implementations, the first arm, the second arm, and the third arm may be arranged in a single plane.

In some example implementations of the nerve probe assembly of any preceding example implementation, or any combination of any preceding example implementations, the second arm may be arranged between the first arm and the third arm, the adjustment structure may be coupled to the second arm to adjust the distance between the respective ends of the first and third arms relative to the second arm, and thereby adjust the corresponding distance between the first and third electrodes relative to the second electrode.

In some example implementations of the nerve probe assembly of any preceding example implementation, or any combination of any preceding example implementations, the adjustment structure may include a spatial positioning mechanism coupled between the second arm and each of the first arm and the third arm to adjust the distance between the respective ends of the first and third arms relative to the second arm, and thereby adjust the corresponding distance between the first and third electrodes relative to the second electrode, and wherein adjustment of the adjustment structure may correspondingly adjust the spatial positioning mechanism.

In some example implementations of the nerve probe assembly of any preceding example implementation, or any combination of any preceding example implementations, the adjustment structure may be translatable to a plurality of positions including: an extended position in which the distance between the respective ends of the first and third arms relative to the end of the second arm may be at a maximum distance and the corresponding distance between the first and third electrodes relative to the second electrode is at a maximum distance, a retracted position in which the distance between the respective ends of the first and third arms relative to the end of the second arm may be at a minimum distance and the corresponding distance between the first and third electrodes relative to the second electrode is at a minimum distance, and at least one intermediate position between the extended position and the retracted position, in which the distance between the respective ends of the first and third arms relative to the end of the second arm may be at an intermediate distance and the corresponding distance between the first and third electrodes relative to the second electrode is at an intermediate distance, the intermediate distances being between the maximum and minimum distances.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURE(S)

Figure 9A:
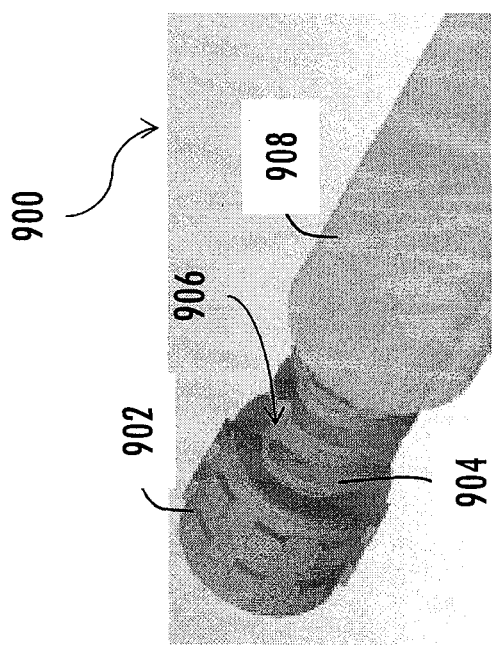
Figure 9B:
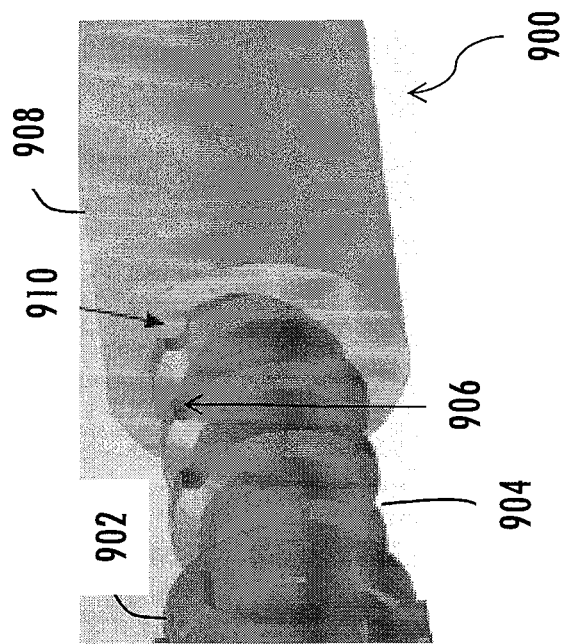
Figure 10A:
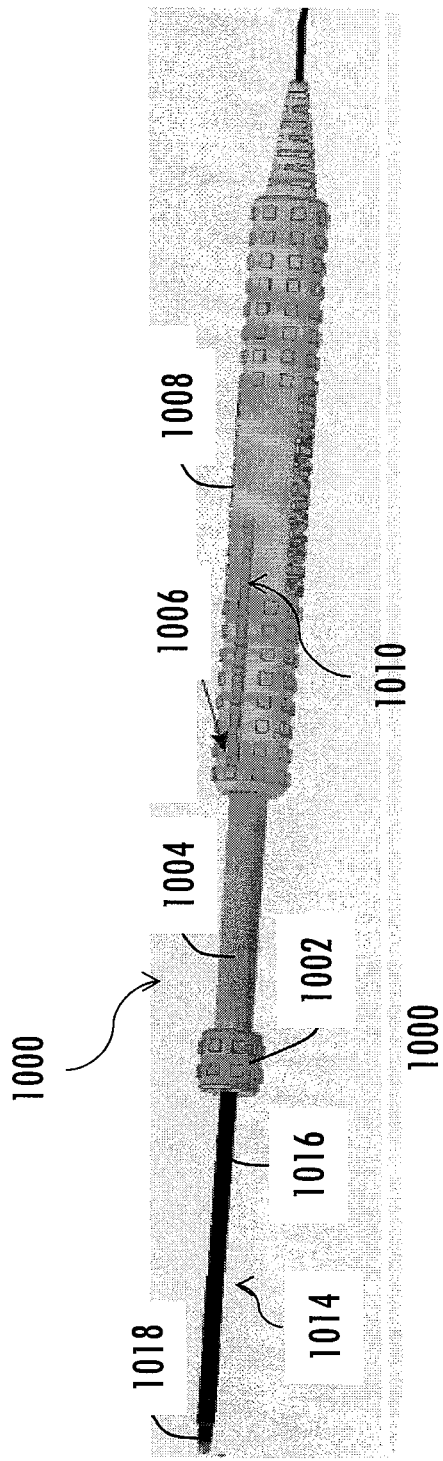
Figure 10B:
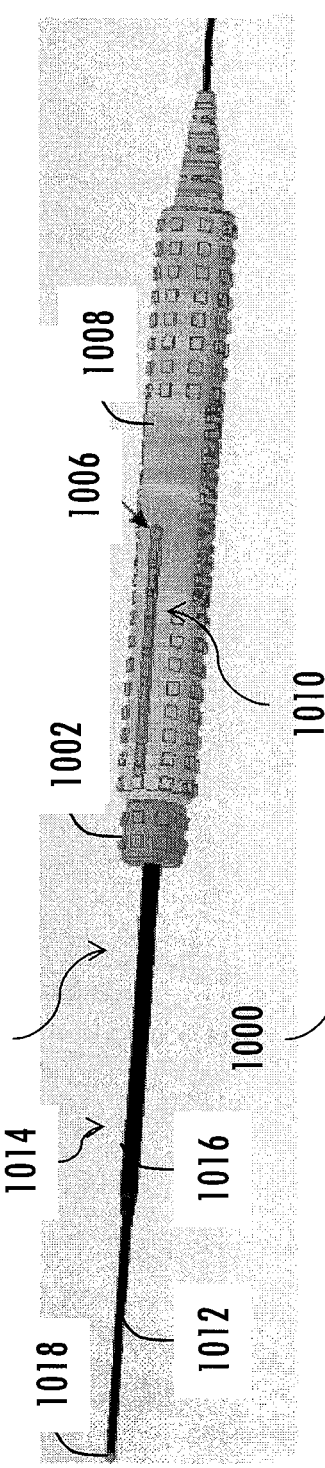
Figure 10C:
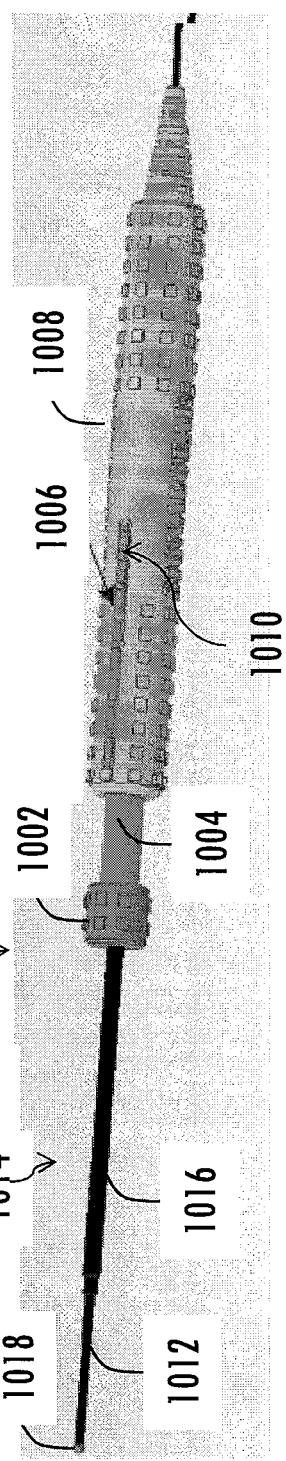

Having thus described the disclosure in general terms, reference will now be made to the accompanying figures, which are not necessarily drawn to scale, and wherein:

FIG. 1 illustrates a schematic of an example nerve probe assembly for electrically stimulating tissue or recording stimulated tissue activity according to example implementations of the present disclosure;

FIGS. 2A, 2B, and 2C illustrate different example wire configurations for axial lengths of electrical probes for a nerve probe assembly according to example implementations of the present disclosure;

FIGS. 3A, 3B, and 3C illustrate different example configurations of shapeable parts of electrical probes for a nerve probe assembly according to example implementations of the present disclosure;

FIGS. 4A, 4B, 4C, 4D, 4E and 4F illustrate different example electrodes disposed on or about an end of an electrical probe for a nerve probe assembly according to example implementations of the present disclosure;

FIGS. 5A, 5B, 5C, 5D, 5E, 5F, and 5G illustrate different example configurations of electrically-insulating sheathings on axial lengths of electrical probes and electrodes for a nerve probe assembly according to example implementations of the present disclosure;

FIGS. 6A, 6B, and 6C illustrate different views of a back-drive nerve probe assembly according to example implementations of the present disclosure;

FIGS. 7A, 7B, 7C, and 7D illustrate different views of a front-drive nerve probe assembly according to example implementations of the present disclosure;

FIGS. 8A, 8B, and 8C illustrate different shapes of rigid sheathings of a front-drive nerve probe assembly according to example implementations of the present disclosure;

FIGS. 9A and 9B illustrate different views of an indexing mechanism coupled to or integrated with an adjustment structure of a nerve probe assembly according to example implementations of the present disclosure;

FIGS. 10A, 10B, and 10C illustrate different views of another indexing mechanism coupled to or integrated with an adjustment structure of a nerve probe assembly according to example implementations of the present disclosure; and FIGS. 11A and 11B illustrate different views of a multipole nerve probe assembly according to example implementations of the present disclosure.

DETAILED DESCRIPTION

Some implementations of the present disclosure will now be described more fully hereinafter with reference to the accompanying figures, in which some, but not all implementations of the disclosure are shown. Indeed, various implementations of the disclosure may be expressed in many different forms and should not be construed as limited to the implementations set forth herein; rather, these example implementations are provided so that this disclosure will be thorough and complete, and will fully convey the scope of the disclosure to those skilled in the art. As used herein, the term "and/or" and the "/" symbol includes any and all combinations of one or more of the associated listed items. Also, for example, reference may be made herein to quantitative measures, values, relationships or the like. Unless otherwise stated, any one or more if not all of these may be absolute or approximate to account for acceptable variations that may occur, such as those due to engineering tolerances or the like.

Further, unless otherwise indicated, something being described as being a first, second or the like should not be construed to imply a particular order. It should be understood that the terms first, second, etc. may be used herein to describe various steps, calculations, positions and/or the like, these steps, calculations or positions should not be limited to these terms. These terms are only used to distinguish one operation, calculation, or position from another. For example, a first position may be termed a second position, and, similarly, a second step may be termed a first step, without departing from the scope of this disclosure. Additionally, something may be described as being above something else (unless otherwise indicated) may instead be below, and vice versa; and similarly, something described as being to the left of something else may instead be to the right, and vice versa. As used in the specification, and in the appended claims, the singular forms "a," "an," "the," include plural referents unless the context clearly dictates otherwise. Like reference numerals refer to like elements throughout.

Example implementations of the present disclosure provide an electrical probe assembly for electrically stimulating an object or recording stimulated object activity. Generally, the electrical probe assembly may include at least an electrical probe. Where the As used herein, an "electrical probe," "nerve probe," and the like may refer to either a stimulus (stim) probe that uses electrical energy to stimulate (innervate) an object, or a recording probe that records activity (e.g., electrical signals, such as a reflex arc or a reflex pathway), which may result from electrically stimulating the object. Notably, where tissue is the object to be stimulated or recorded, the electrical probe assembly disclosed herein is referred to as a "nerve probe assembly," although "nerve probe assembly" and "electrical probe assembly" may be used interchangeably.

As used herein, an "object" may refer to tissue such as human, non-human animal or plant tissue. This includes human or non-human animal tissue, such as, for example, connective tissue, muscle tissue, nervous tissue, and epithelial tissue. Plant tissue includes, such as, for example, meristematic tissue and permanent tissue. In other examples, an "object" may refer to an electrically-conductive inorganic material, such as, for example, a glass, a ceramic, and a metal. Any other type of material that may be electrically-conductive or can produce an electrical signal can also be considered an "object" as used in this disclosure.

In some example implementations, an electrical probe assembly advantageously is adaptable for electrically-stimulating objects or recording stimulated object activity in various different environments. As such, the electrical probe may include an electrode disposed about an end thereof. The electrical probe may define an axial length that comprises a conductive material, while the electrode may likewise comprise a conductive material.

The axial length of the electrical probe may include a shapeable part. As used herein, "shapeable" or "shapeability" refers to an ability of the shapeable part of the axial length of the electrical probe to be manually manipulated into different configurations (e.g., shapes). The shapeable part of the axial length of the electrical probe (or more simply, the shapeable part of the electrical probe) may be pliant, such that the shapeable part is easily manipulated by a user (e.g., a human user, a robotic user, or the like) into one or more different shapes. After manipulation into a first shape, the shapeable part may remain in the first shape until the user manipulates the shapeable part into subsequent different shapes, such as a second shape, a third shape, a fourth shape, etc. The shapeable part may then be manipulated back to the first shape or any previous shapes.

The shapeable part of the electrical probe may also be adaptable for different flexibilities, ranging from "stiff" to "flexible." "Flexible," "flexibility," etc., refers to how the shapeable part of the electrical probe reacts to a non-axial force. A "stiff" shapeable part of the electrical probe may be a shapeable part that may experience zero deflection under zero force (i.e., is rigid or stiff); although, some degree of non-axial force may introduce some resultant deflection of the shapeable part.

By contrast, a "flexible" shapeable part of the electrical probe may be a shapeable part that may exhibit a degree of deflection through minimal non-axial force. The flexibility of the shapeable part of the electrical probe may be modified by an adjustment structure that adjusts exposure of the axial length of the electrical probe relative to a rigid sheathing that may cover at least a portion of the shapeable part of the electrical probe. Increased exposure of the axial length of the electrical probe relative to the rigid sheathing may increase a degree of deflection of the shapeable part from non-axial force, while decreased exposure of the axial length of the electrical probe relative to the rigid sheathing may decrease a degree of deflection of the shapeable part from non-axial force.

Accordingly, for purposes of the present disclosure, shapeability of the shapeable part of the electrical probe refers to variations of the shape of the shapeable part, while flexibility of the shapeable part of the electrical probe refers to variations of the degree of deflection of the shapeable part in response to non-axial force.

In some example implementations, the nerve probe assembly may include more than one electrical probe, such as two, three, four, five, etc., electrical probes. The multiple electrical probes may each include an electrode disposed about respective ends thereof. A handle may include a corresponding number of arms adapted to carry the electrical probes. As such, the multiple electrical probes may be carried in respective arms in a single plane or may be carried in different planes. A spatial distance between the electrodes of each of the electrical probes may be adjusted by a spatial positioning mechanism, which may be coupled to the handle or one or more of the number of arms. An adjustment structure may also be coupled to the handle or one or more of the numbers such that adjustment of the adjustment structure may correspondingly adjust the spatial positioning mechanism.

Accordingly, the nerve probe assembly disclosed herein may perform the role of multiple, different nerve probe assemblies since the nerve probe assembly disclosed herein is shapeable, flexible, and/or multipolar to meet a variety of electrical-stimulation and/or recordation needs. As such, the nerve probe assembly may be utilized in applications such as surgeries, electrotherapies, electromyogram (EMG) biofeedback procedures, and the like, so as to advantageously, for example, electrically-stimulate tissue and/or record electrically-stimulated tissue activity, which otherwise may not be reachable by a straight-shafted electrical probe, electrically stimulate multiple areas of tissue at one time and/or record activity of the stimulated multiple areas of tissue at one time, limit electrical-conductivity to where tissue is disposed, thereby decreasing the need for excessive movement (e.g., lifting) of anatomical obstacles such as nerves and potentially decreasing risk for stretching the anatomical obstacle, and the like.

Referring now to FIG. 1, a schematic of an example electrical probe assembly 100 for electrically stimulating an object or recording stimulated activity of an object, such as tissue 102, is illustrated according to example implementations of the present disclosure. The electrical probe assembly may comprise an electrical probe 104 including an electrode 106 disposed on or about an end thereof. The nerve probe assembly may comprise more than one electrical probe, such as, for example, two electrical probes including first and second electrodes disposed on or about respective ends thereof, three electrical probes including first, second, and third electrodes disposed on or about respective ends thereof, etc.

In some example implementations, an axial length of the electrical probe may include a shapeable part 108. The shapeable part may be shapeable into different shapes, such as, for example, a straight shape, an angled shape, and the like. As such, the shapeable part may comprise a material that allows a user to manually manipulate the shapeable part into a first shape, a second shape, a third shape, etc., where the shapeable part remains in that shape until further manipulation into subsequent different shapes. For example, after manipulation of the shapeable part into a first shape, the shapeable part may remain in the first shape until the user manipulates the shapeable part into a second shape, a third shape, a fourth shape, etc. The shapeable part may then be manipulated back to the first shape or any previous shapes.

In some example implementations, the electrical probe 104 may comprise wire extending along the axial length thereof. The wire of the electrical probe may include one or more strands of wire (e.g., lead wire). There may be one wire, two strands of wire, three strands of wire, four strands of wire, etc., which may be wound together. The strands of wire may comprise an electrically-conductive material, such as, but not limited to platinum iridium, stainless steel, gold-plated silver, and the like. The strands of wire may be covered in a similar, electrically-conductive material, which may vary in composition along the axial length of the electrical probe. For example, a rigid part of the electrical probe may comprise the strands of wire covered in a non-pliant, electrically-conductive material such that the rigid part cannot be easily shaped, while the shapeable part 108 may comprise electrically-conductive wire covered in a pliant, electrically-conductive material such that the shapeable part may be easily shaped into different shapes.

FIGS. 2A-2C illustrate different example wire configurations for axial lengths of electrical probes, 200A-200C, for a nerve probe assembly, such as the nerve probe assembly 100. In FIG. 2A, for example, an axial length of a shapeable portion 202A is illustrated, with three (3) strands of wire 204A wound together and with a single electrode 206A defining a ball tip electrode at the end thereof. In FIG. 2B, for example, an axial length of a shapeable portion 202B is illustrated, with seven (7) strands of wire 204B wound together and with a single electrode 206B defining a ball tip electrode at the end thereof. In FIG. 2C, for example, an axial length of a shapeable portion 202C is illustrated, with nineteen (19) strands of wire 204C wound together and with a single electrode 206C defining a ball tip electrode at the end thereof.

In some example implementations, the strands of wire extending through the shapeable part 108 of the electrical probe 102 may be split into groups of one or more strands of wire each, where each group may be individually shapeable. The groups of wire may be bonded together (e.g., with a heat shrink) along an axial length of the electrical probe. For example, the groups of wire may be bonded along the shapeable part, and may be separable beginning from the end of the electrical probe where the electrode is disposed, so that the electrodes of each group of the one or more wires may be separated at a distance from one another. In this manner, a user may be able to make small adjustments to a shape of the shapeable part by adjusting a shape of each group of the one or more wires.

FIGS. 3A-3C illustrate different example configurations of shapeable parts 300A-300C of an electrical probe assembly, such as the nerve probe assembly 100, where the shapeable parts are each split into groups of one or more strands of wire each. In FIG. 3A, the shapeable part 300A is split into two groups of one or more strands of wire 302A, 304A, which are bonded along an axial length of an electrical probe 306A and are separated beginning from an end of the electrical probe where electrodes 308A are disposed to about midway along an axial length of the shapeable part. In FIG. 3B, the shapeable part 300B is split into two groups of one or more strands of wire 302B, 304B, which are bonded along an axial length of an electrical probe 306B and are separated beginning from an end of the electrical probe where electrodes 308B are disposed to about three quarters of the way along an axial length of the shapeable part. The axial length of the shapeable part in FIG. 3B is shorter than the axial length of the shapeable part in FIG. 3A.

In FIG. 3C, the shapeable part 300C is split into two groups of one or more strands of wire 302C, 304C, which are bonded along an axial length of an electrical probe 306C and are separated beginning from an end of the electrical probe where electrodes 308C are disposed about midway along an axial length of the shapeable part. The axial length of the shapeable part in FIG. 3C is shorter than the axial length of the shapeable part 300A in FIG. 3A, and about a same or substantially a same length of the shapeable part 300B in FIG. 3B.

A spacer 310 is provided along the axial length of the shapeable part 300C in FIG. 3C and may be coupled to each of the two groups of one or more strands of wire 302C, 304C. The spacer may assist in retaining the separation between the groups so that the corresponding distance between the electrodes 308C is maintained. However, translating the spacer along the axial length of the electrical probe 306C may increase or decrease the separation between the electrodes of each group. For example, where the spacer is moved along an axial length of the electrical probe away from the end thereof, the separation between the electrodes of each group of one or more wires may be increased. In another example, where the spacer is moved along an axial length of the electrical probe toward the end thereof, the separation between the electrodes of each group of one or more wires may be decreased.

Referring back to FIG. 1, the electrode 106 may be disposed on or about an end of the electrical probe 104 so that the electrode is disposed on or about an end of the shapeable part 108. The strands of wire extending through the axial length of the electrical probe may connect the electrode to at least one cathode (e.g., three cathodes) and at least one anode (e.g., two anodes) of an electrical power source (e.g., a battery) so as to conduct electrical current through the strands of wire extending along the axial length of the electrical probe to the electrode.

The electrode 106 may define a single electrode (monopolar) or may define two or more electrodes (multipolar) in various arrangements. For example, the electrode may define two electrodes, three electrodes, four electrodes, etc. Where there are multiple electrodes, at least one of the electrodes may comprise a stimulation electrode to stimulate an object, such as tissue, while at least another one of the electrodes may comprise a recording electrode to record activity of a stimulated object, such as tissue. A stimulating tip may be configured to electrically innervate or communicate electrical energy to an object, such as tissue. A recording tip may be configured to record a reflex arc or a reflex pathway that results from electrically stimulating the object.

In some example implementations, the electrode may include one or more stimulating tips. For example, an electrode defining a first stimulating tip (monopolar) may be utilized for stimulating an object, such as tissue, such that the first stimulating tip is a first pole, which references another electrode separate from the stimulation probe assembly (i.e., is a second pole). In another example, an electrode defining first and second stimulating tips (bipolar) may utilize the first stimulating tip as an anode and the second stimulating tip as a cathode, or vice versa. In a still further example, an electrode defining first, second, and third stimulating tips (pseudo bipolar) may utilize the first and third stimulating tips as a combined anode and the second stimulating tip as a cathode. Other combinations are also contemplated herein, such as electrodes defining both recording and stimulating tips, only recording tips, etc.

The electrode 106 may comprise an electrically-conductive material, which may be the same material or a different material from the electrically-conductive material covering the axial length of the electrical probe. The electrically-conductive material of the electrode may thus comprise, but is not limited to, platinum iridium, stainless steel, gold-plated silver, and the like.

FIGS. 4A-4F illustrate different example electrodes 400A-400F disposed on or about an end of electrical probes for a nerve probe assembly, such as the nerve probe assembly 100. In FIG. 4A, a single electrode 400A is shaped as a sphere (i.e., a ball tip electrode). In FIG. 4B, a single electrode 400B is shaped to be flush with an end of an electrical probe (i.e., a flush tip electrode). In FIG. 4C, a single electrode 400C is shaped as a cylinder with a domed top (i.e., a rounded tip electrode). In FIG. 4D, two electrodes 400D are shaped to be flush with an end of an electrical probe and are arranged in concentric circles (i.e., a concentric bipolar tip electrode). In FIG. 4E, two electrodes 400E are shaped as cylinders with domed tops and are linearly arranged adjacent to one another (i.e., a side-by-side bipolar tip electrode). In FIG. 4F, three electrodes 400F are shaped as cylinders with domed tops and are linearly arranged adjacent to one another (i.e., a side-by-side tripolar tip electrode).

Other electrode configurations not illustrated in FIGS. 4A-4F are also contemplated by this disclosure. One example implementation by may include two stimulating electrodes arranged in concentric circles on or about an end of an electrical probe and two or more recording electrodes extending on or about an end of the electrical probe or on or about an axial length of the electrical probe.

Referring back to FIG. 1, the electrical probe 104 may comprise an electrically-insulating sheathing 110 that extends along or at least partially along the electrical probe. The electrically-insulating sheathing may comprise a material whose internal electrical charges do not flow freely so that very little electrical current flows through it under the influence of an electric field. The electrically-insulating sheathing may, thus, comprise a material such, as for example, glass, paper, polymers, plastics, and the like.

In some example implementations, the electrically-insulating sheathing 110 may extend along the axial length of the electrical probe 104 up to but not including the end of the electrical probe so that only the electrode 106 is exposed. As used herein, "expose" refers to electrical current being allowed to flow freely or not be inhibited by any insulating material, so that the electrical current can be transferred. In another example, the electrically-insulating sheathing may extend along the axial length of the electrical probe up to and including the end of the electrical probe, and around the electrode so that only the electrode is exposed. The electrically-insulating sheathing may define an opening or a window so that the exposed portion of the axial length of the electrical probe defines the electrode for electrically stimulating the tissue or recording activity of the stimulated tissue.

FIGS. 5A-5F illustrate different example configurations of electrically-insulating sheathings 500A-500F on axial lengths of electrical probes and electrodes of electrical probes for a nerve probe assembly, such as nerve probe assembly 100. FIG. 5A illustrates an electrically-insulating sheathing 500A that extends along an axial length of an electrical probe 502A up to the electrode 504A shaped as a crook so that only the electrode is exposed.

FIGS. 5B-5F illustrate an electrically-insulating sheathing that defines an opening or window defining an exposed part of an electrical probe, with an end shaped as a crook or hook, to thereby define an electrode of the electrical probe. This may be advantageous when a user elevates an object (e.g., nerves) from surrounding objects (e.g., tissues). One of the primary reasons users may utilize a crooked electrical probe to elevate nerves is to electrically isolate the nerve from the surrounding tissue in order to stimulate that nerve without electrically activating the surrounding tissue. However, elevating nerves by lifting them with a conventional crooked electrode may stretch the nerve. The electrically-insulating sheathing that defines an opening or window about an electrical probe with an end shaped as a crook or hook, as disclosed herein, advantageously enables a user to mechanically hold and elevate tissue a minimal amount without stimulating said tissue, while electrically stimulating only what is underneath the tissue being held. As such, the disclosed configuration may decrease the amount of elevation required to electrically isolate the nerve beneath the tissue, thereby potentially decreasing the risk for nerve injury due to nerve stretching.

FIG. 5B illustrates an electrically-insulating sheathing 500B that extends along an axial length of an electrical probe 502B shaped as a crook. In this manner, the electrically-conductive sheathing in FIG. 5B defines an electrode 504B via an opening or a window 506B in the electrically-insulating sheathing. The opening exposes the electrode defined thereby about an interior portion of the crook.

FIGS. 5C and 5D illustrate two different configurations of electrically-insulating sheathing 500C and 500D (respectively) that extend along axial lengths of electrical probes 502C and 502D shaped as crooks. In this manner, the electrically-conductive sheathing defines electrodes 504C, 504D via openings 506C, 506D in the electrically-insulating sheathings. The openings expose the electrode defined thereby. The electrodes in FIGS. 5C and 5D are smaller than the electrode 504B illustrated in FIG. 5B. In FIG. 5C, the opening is located on an interior portion of the crook, closer to an end of the electrical probe, while in FIG. 5D, the opening is located on an interior portion of the crook, farther away from the end of the electrical probe.

FIG. 5E illustrates an electrically-insulating sheathing 500E that extends along an axial length of an electrical probe 502E shaped as a crook. In this manner, the electrically-conductive sheathing in FIG. 5E defines an electrode 504E via an opening or window 506E in the electrically-insulating sheathing. The opening or window is located on an exterior portion of the crook.

FIG. 5F illustrates an electrically-insulating sheathing 500F that extends along an axial length of an electrical probe 502F shaped as a crook. In this manner, the electrically-conductive sheathing in FIG. 5F defines an electrode 504F via an opening or window 506F in the electrically-insulating sheathing. The opening or window is located on an interior portion of the crook. The electrode of FIG. 5F is larger than that illustrated in FIGS. 5B-5E.

FIG. 5G illustrates an electrically-insulating sheathing 500G that extends along an axial length of an electrical probe 502G shaped as a straight shape. In this manner, the electrically-conductive sheathing in FIG. 5G defines an electrode 504G via an opening 506G in the electrically-insulating sheathing. The window or opening is located on an interior portion of the straight shape. The electrode in FIG. 5G is smaller than that illustrated in FIGS. 5B-5F.

Returning back to FIG. 1, the nerve probe assembly 100 may comprise a rigid sheathing 112 adapted to cover and thereby inhibit a portion of the shapeable part 108 of the axial length of the electrical probe from being shaped, such that the portion of the shapeable part covered by the rigid sheathing is adjustable. More particularly, the axial length of the electrical probe may extend through the rigid sheathing so that at least the electrode 106 is exposed. The rigid sheathing may be considered non-shapeable, non-flexible or stiff, such that it cannot be shaped at all or cannot be easily shaped in comparison with the shapeable part of the electrical probe.

In some example implementations, an adjustment structure 114 and a handle 116 may be affixed to respective ones of the electrical probe 104 and the rigid sheathing 112. The handle may define an internal cavity sized to fit the adjustment structure. In this manner, the adjustment structure may be adapted to cooperate with the handle to enable adjustment of an amount of the adjustment structure that extends out of the handle, and thereby adjustment of the portion of the shapeable part 108 of the axial length of the electrical probe covered by the rigid sheathing. Specific examples of the cooperation of the adjustment structure and the handle to adjust an amount of the adjustment structure that extends out of the handle are illustrated in FIGS. 6A-6C (back-drive nerve probe assembly) and FIGS. 7A-7D (front-drive nerve probe assembly).

In some other example implementations, the adjustment structure 114 may be coupled to one or more portions of the handle 116 (e.g., a first arm or a second arm). In this manner, the adjustment structure may be adapted to enable adjustment of a distance between multiple electrodes 104 (e.g., first and second electrodes). Specific examples of the cooperation of the adjustment structure and the handle to enable adjustment of a distance between multiple electrodes are illustrated in FIGS. 10A and 10B.

The nerve probe assembly 100 may also further comprise an indexing mechanism 118 coupled to or integrated with the adjustment structure 114 and arranged to index the adjustment structure in a plurality of pre-determined positions (i.e., pre-determined increments) relative to the handle 116. The plurality of positions may include an extended position, a retracted position, and at least one intermediate position therebetween. The extended position and the retracted position may be respectively opposing ends of a range of positions that the adjustment structure can be positioned in, with the extended position being the most extended position and the minimum position being the most retracted position that the adjustment structure may be positionable in. Example implementations of an indexing mechanism are illustrated in FIGS. 9A and 9B and 10A-10C.

FIGS. 6A-6C illustrate an example implementation of a nerve probe assembly as generally described in FIG. 1. In FIGS. 6A-6C, the nerve probe assembly 600 is configured as a "back-drive" assembly, where an adjustment structure extends between a plurality of positions between an extended position and a retracted position relative to a back end of a handle.

In FIG. 6A, the nerve probe assembly 600 comprises an electrical probe 602 including an electrode 604 disposed on or about an end thereof for electrically stimulating tissue or recording stimulated tissue activity. The electrode may define a single electrode or two or more electrodes. Where the electrode defines two or more electrodes, the two or more electrodes may include a stimulation electrode for electrically-stimulating tissue, and a recording electrode for recording stimulated tissue activity. Where the electrode defines the two or more electrodes, the two or more electrodes may be arranged as concentric electrodes or side-by-side electrodes.

An axial length of the electrical probe 602 includes a shapeable part 606. The axial length of the electrical probe may also define a stiff portion 608 that is not shapeable or is not easily shapeable as compared to the shapeable part.

In some example implementations, and as illustrated in FIG. 6A, the electrical probe 602 may further include an electrically-insulating sheathing 610 that extends along the axial length of the electrical probe either up to but not including the end of the electrical probe or up to and including the end of the electrical probe and around the electrode 604. As such, the electrically-insulating sheathing may expose only a portion of or a substantial entirety or entirety of the electrical probe so as to define an electrode.

The nerve probe assembly 600 further comprises a rigid sheathing 612 adapted to cover and thereby inhibit a portion of the shapeable part 606 of the axial length of the electrical probe 602 from being shaped. The portion of the shapeable part covered by the rigid sheathing is adjustable so that an amount of the shapeable part not covered by the rigid sheathing is adjusted. In some example implementations, and as illustrated in FIGS. 6B and 6C, at least the electrode 604 of the electrical probe 602 extends out of the rigid sheathing so that at least the electrode is exposed.

The nerve probe assembly still further comprises an adjustment structure 614 and a handle 616. The adjustment structure and the handle are affixed to respective ones of the electrical probe 602 and the rigid sheathing 612. The handle defines an internal cavity sized to fit the adjustment structure such that the handle and the adjustment structure are adapted to cooperate to enable adjustment of an amount of the adjustment structure that extends out of the handle, and thereby adjustment of the portion of the shapeable part 606 of the axial length of the electrical probe covered by the rigid sheathing.

In some example implementations, the electrical probe 602 and the rigid sheathing 612 may be affixed to respectively the adjustment structure 614 and the handle 616. In this manner, the inner cavity of the handle may be arranged to operatively receive the adjustment structure through an end (back end) of the handle, as illustrated for example in FIGS. 6B and 6C. The handle may include a gripping region including, for example, a plurality of protrusions for gripping. As such, the rigid sheathing may be coupled to and in coaxial alignment with an opposing end (front end) of the handle, through which the electrical probe 602 is received. As illustrated in FIGS. 6B and 6C, for example, the electrode 604 of the electrical probe extends out of the rigid sheathing so that at least the electrode is exposed relative to the rigid sheathing.

In some example implementations, the adjustment structure 614 may comprise a threaded insert including or defining a plurality threads. The handle 616 may comprise a corresponding interior thread adapted to threadably engage the threaded insert. For example, the corresponding interior thread of the handle may extend from the end (back end) of the handle so that the threaded insert received through the back end of the handle is threadably engaged with the corresponding thread of the handle. Specifically, and as illustrated in FIGS. 6B and 6C, the threaded insert extends from a back end of the handle, so that the nerve probe assembly is considered to be "back-driven."

The threaded insert of the adjustment structure 614 may be rotatable within the internal cavity with the corresponding interior thread to adjust the amount of the threaded insert that extends out of the handle 616, and thereby adjust the portion of the shapeable part 606 of the axial length of the electrical probe 602 covered by the rigid sheathing 612. The threaded insert may be rotatable to a plurality of positions. FIG. 6B and FIG. 6C illustrate the threaded insert in a retracted position (FIG. 6B) and an extended position (FIG. 6C) relative to the end (back end) of the handle.

In FIG. 6B, the threaded insert is rotated to the retracted position in which a minimum amount of the threaded insert extends out of the handle 616, and thereby a minimum portion of the shapeable part 606 is covered by the rigid sheathing 612. The minimum amount of the threaded insert that extends out of the handle may be the smallest amount that the threaded insert can extend out of the handle, such that the minimum amount is none or only a de minimis amount of an axial length of the threaded insert. Where the minimum portion of the shapeable part is covered by the rigid sheathing, then a maximum uncovered portion of the shapeable part of the electrical probe 602 and the electrode 604 are exposed relative to the rigid sheathing.

In FIG. 6C, the threaded insert is rotated to the extended position in which a maximum amount of the threaded insert extends out of the handle 616, and thereby a maximum portion of the shapeable part 606 is covered by the rigid sheathing 612. The maximum amount of the threaded insert that extends out of the handle may be the greatest amount that the threaded insert can extend out of the handle, such that the maximum amount is all or substantially all of the of an axial length of the threaded insert. Where the maximum portion of the shapeable part is covered by the rigid sheathing, then only the electrode 604 is exposed relative to the rigid sheathing.

In further example implementations, the plurality of positions further includes at least one intermediate position between the extended position and the retracted position. Rotating the threaded insert to at least one of the intermediate positions may result in the amount that the threaded insert extends out of the handle being between the maximum amount and the minimum amount, and thereby the portion of the shapeable part 606 covered by the rigid sheathing 612 is between the maximum portion and the minimum portion. Where the portion of the shapeable part covered by the rigid sheathing is between the maximum portion and the minimum portion, then a corresponding uncovered portion of the shapeable part and the electrode 604 are exposed relative to the rigid sheathing. As such, the shapeable part may be shapeable to different shapes and more flexible when the threaded insert is rotated to the retracted position or an intermediate position.

In some example implementations, "back-drive" nerve probe assemblies, other than the back-drive nerve probe assembly 600 illustrated in FIGS. 6A-6C are also contemplated by the present disclosure. For example, a back-drive nerve probe assembly may comprise a smooth (unthreaded) insert, which may be slidably received in a back end of a handle.

FIGS. 7A-7D illustrate an example implementation of a nerve probe assembly as generally described in FIG. 1. In FIGS. 7A-7D, the nerve probe assembly 700 is configured as a "front-drive" assembly, where an adjustment structure extends between a plurality of positions between an extended position and a retracted position relative to a front end of a handle.

In FIGS. 7A-7D, the nerve probe assembly 700 comprises an electrical probe 702 including an electrode 704 disposed on or about an end thereof for electrically stimulating tissue or recording stimulated tissue activity. The electrode may define a single electrode or two or more electrodes. Where the electrode defines two or more electrodes, the two or more electrodes may include a stimulation electrode for electrically-stimulating tissue, and a recording electrode for recording stimulated tissue activity. Where the electrode defines the two or more electrodes, the two or more electrodes may be arranged as concentric electrodes or side-by-side electrodes.

An axial length of the electrical probe 702 includes a shapeable part 706. The axial length of the electrical probe may also define a stiff portion 708 that is not shapeable or is not easily shapeable as compared to the shapeable part.

Figure 7A:
Figure 7B:
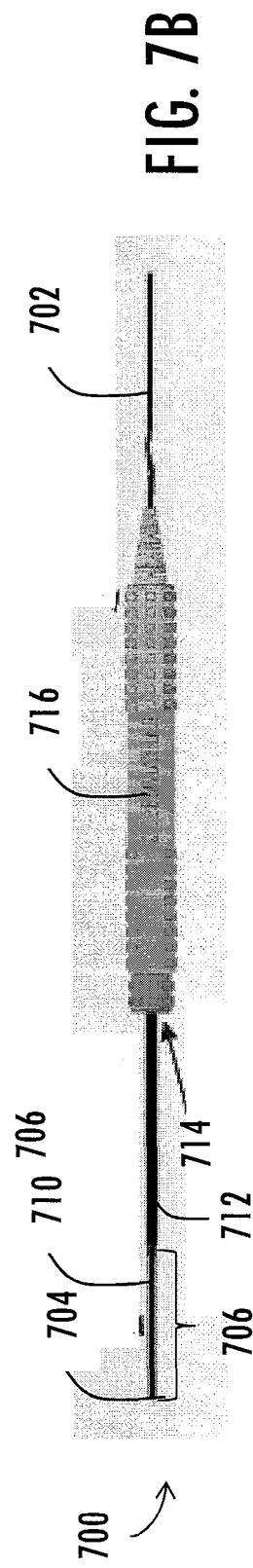
Figure 7C:
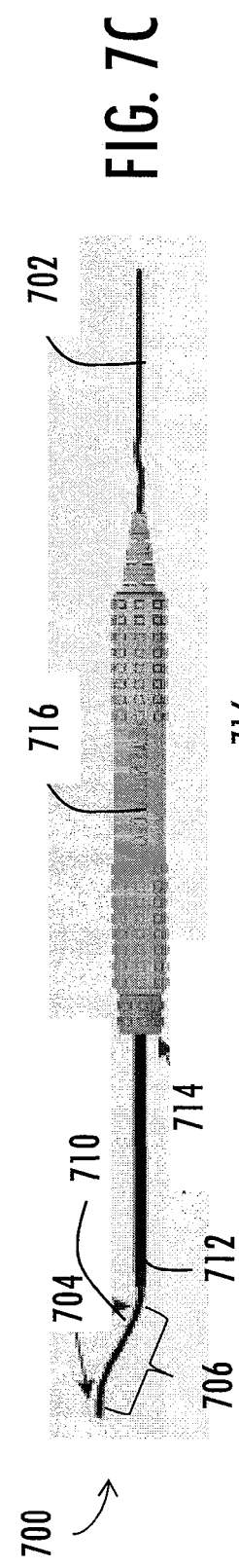

In some example implementations, and as illustrated in FIGS. 7B and 7C, the electrical probe 702 may include an electrically-insulating sheathing 710 that extends along the axial length of the electrical probe either up to but not including the end of the electrical probe or up to and including the end of the electrical probe and around the electrode 704. As such, the electrically-insulating sheathing may expose only a portion of or a substantial entirety or entirety of the electrical probe so as to define an electrode.

Figure 7D:
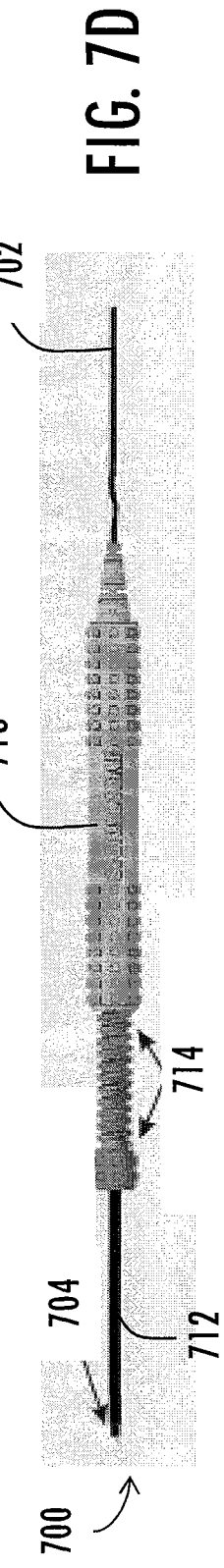

The nerve probe assembly 700 further comprises a rigid sheathing 712 adapted to cover and thereby inhibit a portion of the shapeable part of the axial length of the electrical probe 702 from being shaped. The portion of the shapeable part covered by the rigid sheathing is adjustable. In some example implementations, and as illustrated in FIGS. 7B-7D, at least the electrode 704 of the electrical probe 702 extends out of the rigid sheathing so that at least the electrode is exposed.

The nerve probe assembly still further comprises an adjustment structure 714 and a handle 716. The adjustment structure and the handle are affixed to respective ones of the electrical probe 702 and the rigid sheathing 712. The handle defines an internal cavity sized to fit the adjustment structure such that the handle and the adjustment structure are adapted to cooperate to enable adjustment of an amount of the adjustment structure that extends out of the handle, and thereby adjustment of the portion of the shapeable part 706 of the axial length of the electrical probe covered by the rigid sheathing.

In some example implementations, the electrical probe 702 and the rigid sheathing 712 may be affixed to respectively the handle 716 and the adjustment structure 714. In this manner, the internal cavity of the handle may be arranged to operatively receive the adjustment structure 714 through an end (front end) of the handle. The handle may include a gripping region including, for example, a plurality of protrusions for gripping. As such, the rigid sheathing 712 may be coupled to the adjustment structure and may be arranged in coaxial alignment with the handle and the adjustment structure, so that the electrical probe 702 may be fixedly received through an opposing end (back end) of the handle and may extend through the rigid sheathing at the end (front end). As illustrated in FIGS. 7B-7D, for example, the electrode 704 of the electrical probe extends out of the rigid sheathing so that at least the electrode is exposed relative to the rigid sheathing.

In some example implementations, the adjustment structure 714 may comprise a threaded insert including or defining a plurality of threads. The handle 716 may comprise a corresponding interior thread adapted to threadably engage the threaded insert. For example, the corresponding interior thread of the handle may extend from the end (front end) of the handle so that the threaded insert received through the front end of the handle is threadably engaged with the corresponding thread of the handle Specifically, as illustrated in FIGS. 7B-7D, the threaded insert extends from a front end of the handle, so that the nerve probe assembly is considered to be "front-driven."

The threaded insert of the adjustment structure 714 may be rotatable within the internal cavity with the corresponding interior thread to adjust the amount of the threaded insert that extends out of the handle 716, and thereby adjust the portion of the shapeable part 706 of the axial length of the electrical probe 702 covered by the rigid sheathing 712. The threaded insert may be rotatable to a plurality of positions. FIGS. 7B-7D illustrate the threaded insert in a retracted position (FIGS. 7B and 7C) and an extended position (FIG. 7D) relative to the end (front end) of the handle.

Notably, in the retracted position, the shapeable part 706 is shapeable to different shapes and is more flexible because a maximum portion of the shapeable part is uncovered by the rigid sheathing 712. However, in some example implementations, the rigid sheathing itself may be pre-shaped, such that the shapeable part conforms to the pre-shaped rigid sheathing. FIGS. 8A-8C illustrate different shapes of rigid sheathings of a front-drive nerve probe assembly 800A-800C, similar to the front-drive nerve probe assembly 700. However, the shapes illustrated in FIGS. 8A-8C may be applicable to any nerve probe assembly disclosed herein, where a rigid sheathing is utilized to inhibit a portion of a shapeable part of an axial length of an electrical probe from being shaped.

For example in FIG. 8A, a rigid sheathing 802A of an electrical probe is in a first shape (straight shape), such that a shapeable part is also in a straight shape. A straight shape may be a rigid sheathing/shapeable part that is in coaxial alignment with a handle of an electrical probe. In another example in FIG. 8B, a rigid sheathing 802B of an electrical probe is in a second shape (angled shape), such that a shapeable part is also in an angled shape. An angled shape may be a rigid sheathing/shapeable part that is in non-coaxial alignment with an axial length of a handle, i.e., the rigid sheathing/shapeable part is angled relative to an axial length of the handle In a still further example in FIG. 8C, the rigid sheathing 802C of an electrical probe is in a third shape (bayonet shape), such that a shapeable part is also in a bayonet shape. A bayonet shape may be a rigid sheathing/shapeable part that is bent twice relative to an axial length of a handle, so that both bends of the rigid sheathing/shapeable part result in the rigid sheathing/shapeable part being in non-coaxial alignment with an axial length of the handle in two places. However, any other shape of a rigid sheathing/shapeable part of an electrical probe is also contemplated herein, such as, for example, a hooked shape, a curved shape, etc.

Returning to FIGS. 7A-7D, in FIGS. 7B and 7C, the threaded insert 714 is rotated to the retracted position in which a minimum amount of the threaded insert extends out of the handle 716, and thereby a minimum portion of the shapeable part 706 is covered by the rigid sheathing 712. The minimum amount of the threaded insert that extends out of the handle may be none or only a de minimis amount of the threaded insert. Where the minimum portion of the shapeable part is covered by the rigid sheathing, then a maximum uncovered portion of the shapeable part of the electrical probe 702 and the electrode 604 are exposed relative to the rigid sheathing. In FIG. 7B, the shapeable part is in a first shape (straight shape) and in FIG. 7C, the shapeable part is in a second shape (angled shape).

In FIG. 7D, the threaded insert 714 is rotated to the extended position in which a maximum amount of the threaded insert extends out of the handle 716, and thereby a maximum portion of the shapeable part 706 is covered by the rigid sheathing 712. The maximum amount of the threaded insert that extends out of the handle may be all or substantially all of the of the threaded insert. Where the maximum portion of the shapeable part is covered by the rigid sheathing, then only the electrode 704 is exposed relative to the rigid sheathing. In further example implementations, the plurality of positions further includes at least one intermediate position between the extended position and the retracted position. Rotating the threaded insert to the at least one intermediate position may result in the amount that the threaded insert extends out of the handle being between the maximum amount and the minimum amount, and thereby the portion of the shapeable part 706 covered by the rigid sheathing 712 is between the maximum portion and the minimum portion. Where the portion of the shapeable part covered by the rigid sheathing is between the maximum portion and the minimum portion, then a corresponding uncovered portion of the shapeable part and the electrode 704 are exposed relative to the rigid sheathing. As such, the shapeable part may be shapeable to different shapes and more flexible when the threaded insert is rotated to the extended position or an intermediate position.

In some example implementations, "front-drive" nerve probe assemblies, other than the front-drive nerve probe assembly 700 illustrated in FIGS. 7A-7D are also contemplated by the present disclosure. For example, a front-drive nerve probe assembly may include a snappable rigid sheathing, where an uncovered portion of a shapeable part of an electrical probe is snapped into or otherwise removeably fixed into a front end of a rigid sheathing. In another example, an adjustment structure may include a smooth (unthreaded) insert, which may be slidably received in a front end of a handle.

Indexing mechanisms may be included, in some example implementations, in nerve probe assemblies, such as the nerve probe assembly 600 in FIGS. 6A-6C (i.e., back-drive nerve probe assemblies) and the nerve probe assembly 700 in FIGS. 7A-7D (i.e., front-drive nerve probe assemblies). Indexing mechanisms may also be included in any other nerve probe assembly contemplated herein. Typical indexing mechanisms may be coupled to or integrated with an adjustment structure and arranged to index the adjustment structure into a plurality of predetermined positions relative to a handle The plurality of predetermined positions may include an extended position, a retracted position, and at least one intermediate position therebetween.

FIGS. 9A and 9B illustrate different views of an indexing mechanism coupled to or integrated with an adjustment structure of a nerve probe assembly 900 according to example implementations of the present disclosure. The nerve probe assembly illustrated in FIGS. 9A and 9B may comprise an adjustment structure 902 that comprises a threaded insert including threads 904. The threads may define respective notches 906 along a length of the threaded insert. The threaded insert illustrated in FIGS. 9A and 9B may be a threaded insert such as that illustrated in FIGS. 6A-6C and 7A-7D.

The nerve probe assembly 900 may also comprise a handle 908 defining a corresponding interior thread adapted to threadably engage the threaded insert. The corresponding interior thread of the handle may define a protrusion 910, such that a notch of the respective notches 906 and the protrusion may be alignable. In some example implementations, the threaded insert 902 of the adjustment structure received through the end of the handle 908 is rotatable within the corresponding interior thread of the handle between adjacent ones of the respective notches 906, which may translate into adjustment of the threaded insert into positions of the plurality of positions, including an extended position, a retracted position, and at least one intermediate position therebetween.

For example, and as illustrated in FIGS. 9A and 9B, the threaded insert 902 extends to an intermediate position out of the handle 908. As can be seen in FIG. 9B, a notch of the notches 906 defined on a thread included between a first end and an opposing second end of the threaded insert is aligned with the protrusion 910 of the handle, such that the threaded insert extends an intermediate amount (i.e., between a maximum and a minimum amount) out of the handle.

FIGS. 10A-10C illustrate different views of an indexing mechanism coupled to or integrated with an adjustment structure of a nerve probe assembly 1000 according to other example implementations of the present disclosure. The nerve probe assembly illustrated in FIGS. 10A-10C may comprise an adjustment structure 1002 that comprises an insert with at least a partially smooth outer surface 1004. A protrusion 1006 may be disposed on the smooth outer surface of the insert. A handle 1008 may define a slot 1010 arranged to receive the protrusion. In this manner, the insert may be receivable through the end (front end or back end) of the handle so that the protrusion is received in the slot. As illustrated in FIGS. 10A-10C, the insert is received through the front end of the handle.

In some example implementations, the insert 1002 received through the end of the handle 1008 is translatable along an axial length of the handle to adjust exposure of the axial length of a shapeable part 1012 of an electrical probe 1014 relative to a rigid sheathing 1016. The insert may, thus, be translatable to a plurality of positions including an extended position and a retracted position, as well as any intermediate positions therebetween.

The insert 1002 may be extendable to an extended position. For example, in FIG. 10A, a maximum amount of the insert extends out of the handle 1008, and the protrusion 1006 contacts a first end of the slot 1010, such that only an electrode 1018 of the electrical probe 1014 is exposed. The insert may also be retractable to a retracted position. In another example, in FIG. 10B, a minimum amount of the insert extends out of the handle, and the protrusion contacts an opposing second end of the slot, such that the electrode and a maximum portion of the shapeable part 1012 is uncovered by the rigid sheathing. The insert may also be positionable into at least one intermediate position between the extended position and the retracted position. In a still further example, in FIG. 10C, an intermediate amount (i.e., between the maximum and minimum amount) of the insert extends out of the handle, and the protrusion is between the first end and the opposing second end of the slot, such that the electrode and a portion of the shapeable part between the maximum portion and the minimum portion is uncovered by the rigid sheathing.

Turning now to FIGS. 11A and 11B, different views of an example implementation of a multipole nerve probe assembly, as generally described in FIG. 1, are illustrated according to example implementations of the present disclosure. In FIGS. 11A and 11B, the nerve probe assembly 1100 is configured as a "multipole" assembly, where three electrical probes are provided, and a distance between respective electrodes of the electrical probes is adjusted. A multipole electrical probe assembly as illustrated in FIGS. 11A and 11B may be useful when it is desirable to stimulate at least two different regions or record stimulated activity of an object, such as tissue.

More particularly, for example, the nerve probe assembly 1100 comprises first and second electrical probes 1102A, 1102B including first and second electrodes 1104A, 1104B disposed on or about respective ends thereof for electrically stimulating tissue or recording stimulated tissue activity. In some example implementations, the nerve probe assembly 1100 may comprise a third electrical probe 1102C including a third electrode 1104C disposed on or about an end thereof. Still further, the nerve probe assembly may comprise at least a fourth, a fifth, a sixth, a seventh, etc., electrical probe. As illustrated in FIGS. 11A and 11B, for example, the nerve probe assembly comprises three electrical probes including the first, second, and third electrodes disposed on or about respective ends.

The first, second, and third electrodes 1104A-1104C may each define a single electrode or two or more electrodes. Where the first, second, and third electrodes each define two or more electrodes, the two or more electrodes may include a stimulation electrode for electrically-stimulating tissue, and a recording electrode for recording stimulated tissue activity. Where the first, second, and third electrodes each define the two or more electrodes, the two or more electrodes may be arranged as concentric electrodes or side-by-side electrodes.

The nerve probe assembly 1100 illustrated in FIGS. 11A and 11B further comprises a handle 1106 including first and second arms 1108A, 1108B adapted to carry respectively the first and second electrical probes 1102A, 1102B. In some example implementations, the first and second arms are separate and distinct arms that are joined at one end and are separate at another end. In this example, the first and second arms include respective ends from which the first and second electrical probes extend, so that at least the first and second electrodes 1104A, 1104B are exposed relative to the respective first and second arms.

In some example implementations, the handle 1106 includes a third arm 1108C adapted to carry the third electrical probe 1102C. Like the first and second arms 1108A, 1108B, the third arm may include an end from which the third electrical probe extends. As illustrated in FIGS. 11A and 11B, the first, second, and third arms may be joined at one end and are separate at another end, so at the respective ends of the first, second, and third arms the electrodes extend and are exposed relative thereto.

In some example implementations, an axial length of at least one of the first, second, and third electrical probes 1102A-1102C may include a shapeable part (not shown) shapeable to different shapes. A rigid sheathing (not shown) may be adapted to cover and thereby inhibit a portion of the shapeable part of the axial length of the first, second, and third electrical probes from being shaped. However, the portion of the shapeable part covered by the rigid sheathing may be adjustable, such that different amounts of corresponding other portions of the shapeable part of the axial length of the first, second, and third electrical probes may be exposed.

FIGS. 11A and 11B illustrate the first, second, and third electrical probes 1102A-1102C in fully retracted positions, so that only the first, second, and third electrodes 1104A-1104C are exposed relative to the respective arms 1108A-1108C. However, adjustment of the first, second, and third electrical probes may expose at least a portion of a shapeable part of the axial length of the first, second, and third electrical probes so that the portion of the shapeable part may be shaped into different shapes, while stiffness of the first, second, and third electrical probes may also be adjusted.

In some example implementations, the first, second, and third electrical probes 1102A-1102C may further include an electrically-insulating sheathing (not shown) that extends along the axial length of one or more of the first, second, and third electrical probes either up to but not including the respective ends of the first, second, and third electrical probes or up to and including the respective ends of the first, second, and third electrical probes and around the first, second, and third electrodes 1104A-1104C. As such, the electrically-insulating sheathing may expose only a portion of or a substantial entirety or entirety of the first, second, and third electrical probes so as to define the first, second, and third electrodes.

In some example implementations, as illustrated in FIGS. 11A and 11B, the first, second, and third arms 1108A-1108C of the handle 1106 are arranged in a single plane, such that the corresponding electrical probes 1102A-1102C are also arranged in a single plane. However, a multipole nerve probe assembly may also be arranged so that the multiple arms of the handle are arranged in one or more different planes, such that the corresponding electrical probes are also arranged in the one or more different planes.

The nerve probe assembly 1100 also comprises an adjustment structure 1110 coupled to the first arm 1108A or the second arm 1108B. The adjustment structure may also be coupled to the third arm 1108C. The adjustment structure is adapted to enable adjustment of a distance between the respective ends of the first and second arms, and thereby adjust a corresponding distance between the first and second electrodes 1104A, 1104B. However, the adjustment structure may also be arranged to adjust at least one of exposure of the axial length of the first and second electrical probes relative to any of the first and second arms.

As illustrated in FIGS. 11A and 11B, the adjustment structure 1110 is arranged between the first arm 1108A and the third arm 1108C, and is coupled to the second arm 1108B to adjust the distance between the respective ends of the first and third arms relative to the second arm, and thereby adjust the corresponding distance between the first and third electrodes 1104A, 1104C relative to the second electrode 1104B.

In order to adjust the distance between the respective ends of the first and third arms relative to the second arm, and thereby adjust the corresponding distance between the first and third electrodes 1104A, 1104C relative to the second electrode 1104B, the adjustment structure 1110 may be adjusted between a retracted position and an extended position. In FIG. 11A, for example, the adjustment structure is provided in a retracted position, so that the adjustment structure is positioned at a minimum distance from the second arm 1108B. In FIG. 11B, the adjustment structure is provided in an extended position, so that the adjustment structure is positioned at a maximum distance from the second arm. The adjustment structure may also be positionable into at least one intermediate position (i.e., between the retracted position and the extended position), which may result in the adjustment structure being positioned at an intermediate distance (i.e., between the minimum distance and the maximum distance) from the second arm.

In some example implementations, and as illustrated in FIGS. 11A and 11B, the adjustment structure 1110 is an axial screw 1112 coupled with the second arm 1108B and arranged in two halves with a sleeve 1114 arranged to receive each of the halves at opposing ends thereof. The sleeve may be a threaded sleeve that threads onto threads defined by the axial screw. Each half of the axial screw may be in coaxial alignment with the second arm. However, the adjustment structure may also comprise other example implementations, such as, for example and not limited to, a center screw mechanism, a side screw mechanism, a slide mechanism, a sleeved screw mechanism, a slotted slide mechanism, a spring mechanism, an alternate spring mechanism, and the like.

The nerve probe assembly 1100 also comprises, in some example implementations, a spatial positioning mechanism 1116A and 1116B, which may be part of or separate from the adjustment structure 1110. As illustrated in FIGS. 11A and 11B, the spatial positioning mechanism is separate from, but adjustable in response to adjustment of the adjustment structure. The spatial positioning mechanism may be coupled between the second arm 1108B and each of the first arm 1108A and the third arm 1108C to adjust a distance between the respective ends of the first and third arms relative to the second arm, and thereby adjust the corresponding distance between the first and third electrodes 1104A, 1104C relative to the second electrode 1104B. As such, and as illustrated in FIGS. 11A and 11B, adjustment of the adjustment structure (e.g., rotation of the sleeve 1114 about the axial screw 1112) correspondingly adjusts the spatial positioning mechanism 1116A and 1116B.

The spatial positioning mechanism 1116A and 1116B in FIGS. 11A and 11B comprises pivotable arms, with the first pivoting arm 1116A being coupled between the first arm 1108A and the second arm 1108B and the second pivoting arm 1116B being coupled between the third arm 1108C and the second arm. However, the spatial positioning mechanism in FIGS. 11A and 11B, is just one example implementation of a spatial positioning mechanism Other spatial positioning mechanisms are contemplated herein, such as, for example and not limited to, flexible arms, pivotable pin arms, flexible spring arms, ramp tips, flexible pivot arms, slotted pin arms, and the like.

In some example implementations, adjustment or translation of the adjustment structure 1110, such as the halves of the axial screw 1112 and the sleeve 1114, into one of a plurality of positions including and in between the retracted position and the extended position relative to the second arm 1108B, results in correspondingly adjusting the spatial positioning mechanism 1116A and 1116B into the same positions.

The retracted position is a position in which a retracted position in the distance between the respective ends of the first and third arms 1108A and 1108C relative to the end of the second arm 1108B is at a minimum distance and the corresponding distance between the first and third electrodes 1104A and 1104C relative to the second electrode 1104B is at a minimum distance. For example, and as illustrated in FIG. 11A, in the retracted position, the sleeve 1114 has been rotated in a first direction about the axial screw 1112 (e.g., clockwise) so as to retract the halves of the axial screw relative to the sleeve. Doing so decreases the distance between the sleeve and the second arm, such that the spatial positioning mechanisms 1116A and 1116B being coupled to the second arm are, thus, pulled into axial alignment with the first arm 1108A and the third arm 1108C. The distance between the first and third arms and relative to the end of the second arm is therefore at a minimum distance and the corresponding distance between the first and third electrodes and relative to the second electrode is at a minimum distance.

The extended position is a position in which the distance between the respective ends of the first and third arms 1108A and 1108C relative to the end of the second arm 1108B is at a maximum distance and the corresponding distance between the first and third electrodes 1104A and 1104C relative to the second electrode 1104B is at a maximum distance. For example, and as illustrated in FIG. 11B, in the extended position, the sleeve 1114 has been rotated in a second direction about the axial screw 1112 (e.g., counterclockwise) so as to extend the halves of the axial screw relative to the sleeve. Doing so increases the distance between the sleeve and the second arm, such that the spatial positioning mechanisms 1116A and 1116B being coupled to the second arm are, thus, pushed out of axial alignment with the first arm 1108A and the third arm 1108C. The distance between the first and third arms relative to the end of the third arm is therefore at a maximum distance and the corresponding distance between the first and third electrodes and relative to the second electrode is at a maximum distance.

The at least one intermediate position is a position between the extended position and the retracted position in which the adjustment structure 1110 is at an intermediate distance from the second arm 1108B such that the distance between the respective ends of the first and third arms 1108A and 1108C relative to the end of the second arm is at an intermediate distance and the corresponding distance between the first and third electrodes 1104A and 1104C relative to the second electrode 1104B is at an intermediate distance. The distances are between the maximum and minimum distances. More particularly, in this example, rotation of the sleeve 1114 in either the first or the second direction about the axial screw 1112 (i.e., clockwise or counter-clockwise) may extend or retract the halves of the axial screw relative to the sleeve. Doing so may increase or decrease the distance between the sleeve and the second arm to an intermediate distance between the minimum distance and the maximum distance, such that the spatial positioning mechanisms 1116A and 1116B being coupled to the second arm are, thus, pushed out of axial alignment with the first arm 1108A and the third arm 1108C. The spatial positioning mechanisms may be at an intermediate angle (non-coaxial) that is less than the maximum angle relative to the axes of the first and third arms. The distance between the first and third arms and relative to the end of the second arm is therefore at an intermediate distance and the corresponding distance between the first and third electrodes and relative to the second electrode is at an intermediate distance.

Many modifications and other implementations of the disclosure set forth herein will come to mind to one skilled in the art to which this disclosure pertain having the benefit of the teachings presented in the foregoing descriptions and the associated figures. Therefore, it is to be understood that the disclosure are not to be limited to the specific implementations disclosed and that modifications and other implementations are intended to be included within the scope of the appended claims Moreover, although the foregoing descriptions and the associated figures describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A nerve probe assembly comprising:
    an electrical probe including an electrode disposed on or about an end thereof for electrically stimulating tissue or recording stimulated tissue activity, an axial length of the electrical probe including a shapeable part;
    a rigid sheathing adapted to cover and thereby inhibit a portion of the shapeable part of the axial length of the electrical probe from being shaped, the portion of the shapeable part covered by the rigid sheathing being adjustable; and
    a handle and an adjustment structure affixed to respective ones of the electrical probe and the rigid sheathing, the handle defining an internal cavity sized to fit the adjustment structure, the handle and the adjustment structure adapted to cooperate to enable adjustment of an amount of the adjustment structure that extends out of the handle, and thereby adjustment of the portion of the shapeable part of the axial length of the electrical probe covered by the rigid sheathing,
    wherein the adjustment structure comprises a threaded insert, and the internal cavity of the handle defines a corresponding interior thread adapted to threadably engage the threaded insert, and
    wherein the threaded insert is rotatable within the internal cavity with the corresponding interior thread to adjust the amount of the threaded insert that extends out of the handle, and thereby adjust the portion of the shapeable part of the axial length of the electrical probe covered by the rigid sheathing.

2. The nerve probe assembly of claim 1, wherein the electrode is shaped as a rounded tip electrode, a flush tip electrode, or a ball tip electrode.

3. The nerve probe assembly of claim 1, wherein the electrode defines a single electrode or two or more electrodes.

4. The nerve probe assembly of claim 3, wherein the electrode defines the two or more electrodes, and the two or more electrodes include a stimulation electrode for electrically-stimulating tissue, and a recording electrode for recording activity of the stimulated tissue.

5. The nerve probe assembly of claim 3, wherein the electrode defines the two or more electrodes, and the two or more electrodes are arranged as concentric electrodes or side-by-side electrodes.

6. The nerve probe assembly of claim 1, wherein the electrical probe includes an electrically-insulating sheathing that extends along the axial length of the electrical probe.

7. The nerve probe assembly of claim 6, wherein the electrode of the electrical probe is disposed on the end of the electrical probe, and the electrically-insulating sheathing extends along the axial length of the electrical probe up to but not including the end so that only the electrode is exposed.

8. The nerve probe assembly of claim 6, wherein the electrode is disposed about the end of the electrical probe, and the electrically-insulating sheathing extends along the axial length of the electrical probe up to and including the end, the electrically-insulating sheathing defining an opening to expose a portion of the axial length of the electrical probe that defines the electrode.

9. The nerve probe assembly of claim 1, further comprising an indexing mechanism coupled to or integrated with the adjustment structure and arranged to index the adjustment structure in a plurality of predetermined positions relative to the handle, including an extended position in which a maximum amount of the adjustment structure extends out of the handle, a retracted position in which a minimum amount of the adjustment structure extends out of the handle, and at least one intermediate position therebetween.

10. The nerve probe assembly of claim 1, wherein the electrical probe and the rigid sheathing are affixed to respectively the handle and the adjustment structure.

11. The nerve probe assembly of claim 1, wherein the electrical probe and the rigid sheathing are affixed to respectively the adjustment structure and the handle.

12. The nerve probe assembly of claim 1, wherein the threaded insert is rotatable to a plurality of positions including an extended position in which a maximum amount of the threaded insert extends out of the handle, and thereby a maximum portion of the shapeable part is covered by the rigid sheathing, and a retracted position in which a minimum amount of the threaded insert extends out of the handle, and thereby a minimum portion of the shapeable part is covered by the rigid sheathing.

13. The nerve probe assembly of claim 12, wherein the plurality of positions further includes at least one intermediate position between the extended position and the retracted position in which the amount of the threaded insert that extends out of the handle is between the maximum amount and the minimum amount, and thereby the portion of the shapeable part covered by the rigid sheathing is between the maximum portion and the minimum portion.

14. A nerve probe assembly comprising:
first and second electrical probes including first and second electrodes disposed on or about respective ends thereof for electrically stimulating tissue or recording stimulated tissue activity;
a handle including first and second arms adapted to carry respectively the first and second electrical probes, the first and second arms including respective ends from which the first and second electrical probes extend; and
an adjustment structure coupled to the first arm or the second arm, and adapted to enable adjustment of a distance between the respective ends of the first and second arms, and thereby adjust a corresponding distance between the first and second electrodes,
further comprising a third arm arranged between the first arm and the second arm, the adjustment structure coupled to the third arm to adjust the distance between the respective ends of the first and second arms relative to the third arm, and thereby adjust the corresponding distance between the first and second electrodes.

15. The nerve probe assembly of claim 14, wherein the adjustment structure includes a spatial positioning mechanism coupled between the third arm and each of the first arm and the second arm to adjust the distance between the respective ends of the first and second arms relative to the third arm, and thereby adjust the corresponding distance between the first and second electrodes, and
wherein adjustment of the adjustment structure correspondingly adjusts the spatial positioning mechanism.

16. The nerve probe assembly of claim 14, wherein the adjustment structure is translatable to a plurality of positions including:
an extended position in which the distance between the respective ends of the first and second arms relative to the end of the third arm is at a maximum distance and the corresponding distance between the first and second electrodes is at a maximum distance,
a retracted position in which the distance between the respective ends of the first and second arms relative to the end of the third arm is at a minimum distance and the corresponding distance between the first and second electrodes is at a minimum distance, and
at least one intermediate position between the extended position and the retracted position, in which the distance between the respective ends of the first and second arms relative to the end of the third arm is at an intermediate distance and the corresponding distance between the first and second electrodes is at an intermediate distance, the intermediate distances being between the maximum and minimum distances.

17. A nerve probe assembly of claim 16 comprising:
first and second electrical probes including first and second electrodes disposed on or about respective ends thereof for electrically stimulating tissue or recording stimulated tissue activity;
a handle including first and second arms adapted to carry respectively the first and second electrical probes, the first and second arms including respective ends from which the first and second electrical probes extend; and
an adjustment structure coupled to the first arm or the second arm, and adapted to enable adjustment of a distance between the respective ends of the first and second arms, and thereby adjust a corresponding distance between the first and second electrodes,
further comprising a third electrical probe including a third electrode disposed on or about an end thereof for electrically stimulating tissue or recording stimulated tissue activity, wherein the handle further includes a third arm adapted to carry the third electrical probe, the third arm including an end from which the third electrical probe extends,
wherein the second arm is arranged between the first arm and the third arm, the adjustment structure is coupled to the second arm to adjust the distance between the respective ends of the first and third arms relative to the second arm, and thereby adjust the corresponding distance between the first and third electrodes relative to the second electrode.

18. The nerve probe assembly of claim 17, wherein the first arm, the second arm, and the third arm are arranged in a single plane.

19. The nerve probe assembly of claim 17, wherein the adjustment structure includes a spatial positioning mechanism coupled between the second arm and each of the first arm and the third arm to adjust the distance between the respective ends of the first and third arms relative to the second arm, and thereby adjust the corresponding distance between the first and third electrodes relative to the second electrode, and
wherein adjustment of the adjustment structure correspondingly adjusts the spatial positioning mechanism.

20. The nerve probe assembly of claim 17, wherein the adjustment structure is translatable to a plurality of positions including:
an extended position in which the distance between the respective ends of the first and third arms relative to the end of the second arm is at a maximum distance and the corresponding distance between the first and third electrodes relative to the second electrode is at a maximum distance,
a retracted position in which the distance between the respective ends of the first and third arms relative to the end of the second arm is at a minimum distance and the corresponding distance between the first and third electrodes relative to the second electrode is at a minimum distance, and
at least one intermediate position between the extended position and the retracted position, in which the distance between the respective ends of the first and third arms relative to the end of the second arm is at an intermediate distance and the corresponding distance between the first and third electrodes relative to the second electrode is at an intermediate distance, the intermediate distances being between the maximum and minimum distances.

* * * * *